(12) United States Patent
Garovoy et al.

(10) Patent No.: US 6,652,855 B1
(45) Date of Patent: Nov. 25, 2003

(54) TREATMENT OF LFA-1 ASSOCIATED DISORDERS WITH INCREASING DOSES OF LFA-1 ANTAGONIST

(75) Inventors: Marvin R. Garovoy, San Anselmo, CA (US); Susan M. Kramer, San Francisco, CA (US); Russell L. Dedrick, Kensington, CA (US); Karen Starko, Hillsborough, CA (US)

(73) Assignees: Genentech, Inc., South San Francisco, CA (US); XOMA Ltd., Berkeley, CA (US)

(*) Notice: Subject to any disclaimer, the term of this patent is extended or adjusted under 35 U.S.C. 154(b) by 0 days.

(21) Appl. No.: 09/936,603

(22) PCT Filed: Mar. 17, 2000

(86) PCT No.: PCT/US00/07189

§ 371 (c)(1),
(2), (4) Date: Feb. 11, 2002

(87) PCT Pub. No.: WO00/56363

PCT Pub. Date: Sep. 28, 2000

Related U.S. Application Data

(60) Provisional application No. 60/273,043, filed on Mar. 2, 2001, provisional application No. 60/125,228, filed on Mar. 19, 1999, and provisional application No. 60/125,351, filed on Mar. 19, 1999.

(51) Int. Cl.[7] .................. A61K 39/395; C07K 16/00; C12P 21/08
(52) U.S. Cl. .................. 424/133.1; 424/134.1; 424/154.1; 424/173.1; 530/388.22; 530/387.3
(58) Field of Search .................. 424/144.1, 130.1, 424/133.1, 143.1, 134.1, 152.1, 153.1, 154.1, 173.1; 530/388.22, 387.1, 387.3

(56) References Cited

U.S. PATENT DOCUMENTS

| 5,002,869 A | 3/1991 | Schlossman et al. |
| 5,071,964 A | 12/1991 | Dustin et al. |
| 6,037,454 A | * 3/2000 | Jardieu et al. |

FOREIGN PATENT DOCUMENTS

| AU | 8815518 | 11/1988 |
| CA | 2008368 | 6/1991 |
| EP | 289949 | 11/1988 |
| EP | 346078 | 12/1989 |
| EP | 379904 | 8/1990 |
| EP | 387668 | 9/1990 |
| WO | WO 88/06592 | 9/1988 |
| WO | WO 90/10652 | 9/1990 |
| WO | WO 90/15076 | 12/1990 |
| WO | WO 91/16927 | 11/1991 |
| WO | WO 91/16928 | 11/1991 |
| WO | WO 91/18011 | 11/1991 |
| WO | WO 94/02175 | 2/1994 |
| WO | WO 94/04188 | 3/1994 |
| WO | WO 98/23761 | 6/1998 |

OTHER PUBLICATIONS

Van Noort JM, Amor S. Cell biology of autoimmune diseases. Int Rev Cytol. 178:127–206, 1998.*

Abramowicz et al., "Release of tumor necrosis factor, interleukin–2, and gamma–interferon in serum after injection of OKT3 monoclonal antibody in kidney transplant recipients" *Transplantation* 47(4):606–608 (Apr. 1989).

Azzawi et al., "Identification of Activated T Lymphocytes and Eosinophils in Bronchial Biopsies in Stable Atopic Asthma" *Am. Rev. Resp. Dis.* 142:1407–1413 (1990).

Bauer et al., "Population pharmacokinetics and pharmacodynamics of the anti CD11a antibody hu1124 in human subjects with psoriasis" *J. Pharmacokinetics and Biopharmaceutics* 27 (4):397–420 (1999).

Benjamin et al., "Mechanisms of Monoclonal Antibody–Facilitated Tolerance Induction: A Possible Role for the CD4 (L3T4) and CD11a (LFA–1) Molecules in Self–Non–Self Discrimination" *European Journal of Immunology* 18:1079–1088 (1988).

Campana et al., "Human leukocyte function–associated antigens on lympho–hemapoietic precursor cells" *European Journal of Immunology* 16(5):537–542 (May 1986).

Cavazzana–Calvo et al., "A phase II trial of partially incompatible bone marrow transplantation for high–risk acute lymphoblastic leukaemia in children: prevention of graft rejection with anti–LFA–1 and anti–CD2 antibodies." *British Journal of Haematology* 93(1):131–138 (Apr. 1996).

Cavazzana–Calvo et al., "Prevention of bone marrow and cardiac graft rejection is an H–2 haplotype disparate mouse combination by an anti–LFA–1 antibody" *Transplantation* 59(11):1576–1582 (Jun. 15, 1995).

Chatenoud et al., "In vivo cell activation following OKT3 administration. Systemic cytokine release and modulation by corticosteroids" *Transplantation* 49(4):697–702 (Apr. 1990).

Chatenoud et al., "Systemic reaction to the anti–T–cell monoclonal antibody OKT3 in relation to serum levels of tumor necrosis factor and interferon–α" *New England J. of Medicine* 320(21):1420–1421 (May 25, 1989).

Cockcroft et al., "Prediction of airway responsiveness to allergen from skin sensitivity to allergen an airway responsiveness to histamine" *Am. Rev. Respir. Dis.* 135:264–267 (1987).

Collins, T., "Adhesion molecules in leukocyte emigration" *Science and Medicine* pp. 28–37 (1995).

(List continued on next page.)

Primary Examiner—Christina Chan
Assistant Examiner—Maher Haddad
(74) Attorney, Agent, or Firm—Lee Tan

(57) ABSTRACT

A method is provided for reducing the occurrence of fever, headache, nausea and/or vomiting associated with administration of a therapeutic compound to a mammal in need therof, comprising administering to the mammal a first conditioning dose of a non-target cell depleting compound which binds to a cell surface receptor on a target mammalian cell; and administering a second therapeutic dose of the compound, wherein the second dose is higher than the first dose.

9 Claims, 10 Drawing Sheets

OTHER PUBLICATIONS

Connolly et al., "Treatment of murine lupus with monoclonal antibodies to lymphocyte function–associated antigen–1: dose–dependent inhibition of autoantibody production and blockade of the immune response to therapy" *Clinical Immunology & Immunopathology* 72(2):198–203 (Aug. 1994).

Corrigan & Kay, "CD4 T–Lymphocyte Activation in Acute Severe Asthma" *Am. Rev. Respir. Dis.* 141:970–977 (1990).

Cosimi et al., "Use of monoclonal antibodies to T–cell subsets for immunologic monitoring and treatment in recipients of renal allografts" *New England J. of Medicine* 305(6):308–314 (Aug. 6, 1981).

Crescioli et al., "Theophylline inhibits early and late asthmatic reactions induced by allergens in asthmatic subjects" *Ann. Allergy* 66:245–251 (Mar. 1991).

Curnow, R., "Clinical experience with CD64–directed immunotherapy. An overview" *Cancer Immunology and Immunotherapy* 45(3–4):210–215 (Nov.–Dec. 1997).

de Fougerolles et al., "Characterization of the function of intercellular adhesion molecule (ICAM)–3 and comparison with ICAM–1 and ICAM–2 in immune responses" *Journal of Experimental Medicine* 179(2):619–629 (Feb. 1, 1994).

Desroches et al., "Regulation and Functional Involvement of Distinct Determinants of Leucocyte Function–Associated Antigen 1 (LFA–1) in T–Cell Activation In Vitro" *Scand. J. Immunol.* 33:277–286 (1991.

Djukanovic et al., "Effect of an Inhaled Coticosteroid on Airway Inflammation and Symptoms in Asthma" *Am. Rev. Respir. Dis.* 145:669–674 (1992).

Dustin and Springer, "Lymphocyte function–associated antigen–1 (LFA–1) interation with intercellular adhesion molecule–1 (ICAM–1) is one of at least three mechanisms for lymphocyte adhesion to cultured endothelial cells" *Journal of Cell Biology* 107(1):321–331 (Jul. 1988).

Dustin and Springer, "Role of lymphocyte adhesion receptors in transient interactions and cell locomotion" *Annual Review of Immunology* 9:27–66 (1991).

Dustin et al., "Induction By IL 1 and Interferon–γ: Tissue Distribution, Biochemistry, and Function of a Natural Adherence Molecule (ICAM–1)" *The Journal of Immunology* 137(1):245–254 (Jul. 1, 1986).

Fekete et al., "Involvement of Lymphocyte Function–Associated Antigen–1 (LFA–1) But Not ICAM–1 in a Radioactive Leukocyte Cell–Mediated Immunity (LA–CMI) Assay" *J. Clin. Lab. Immunol.* 31:145–149 (1990).

First et al., "The effect of indomethacin on the febrile response following OKT3 therapy" *Transplantation* 53(1):91–94 (Jan. 1992).

Fischer et al., "Reduction of Graft Failure by a Monoclonal Antibody (Anti–LFA–1 CD11a) After HLA Nonidentical Bone Marrow Transplantation in Children with Immunodeficiencies, Osteopetrosis, and Fanconi's Anemia" *Blood* 77(2):249–256 (Jan. 15, 1991).

Fischer et al., "Role of the LFA–1 Molecule in Cellular Interactions Required For Antibody Production in Humans" *The Journal of Immunology* 136(9):3198–3203 (May 1, 1986).

Goldman et al., "OKT3–induced cytokine release attenuation by high–dose methylprednisolone" *Lancet* 2(8666):802–803 (Sep. 30, 1989).

Goldstein et al., "A randomized clinical trial of OKT3 monoclonal antibody for acute rejection of cadaveric renal transplants. Ortho Multicenter Transplant Study Group" *New England J. of Medicine* 313(6):337–342 (Aug. 8, 1985).

Gordon et al., "Both anti–CD11a (LFA–1) and anti–CD11b (MAC–1) therapy delay the onset and diminish the severity of experimental autoimmune encephalomyelitis" *Journal of Neuroimmunology* 62(2):153–160 (Nov. 1995).

Gottlieb et al., "Psoriasis is clinically and histologically improved by treatment with a humanized anti–CD11a monoclonal antibody (hu1124): results of a multicenter, multiple ascending dose study" *J. Investigative Dermatology* (abstract only) 112(4):647 (Apr. 1999).

He et al., "Effect of LFA–1 and ICAM–1 antibody treatment on murine corneal allograft survival" *Invest. Opthalmol. Vis. Sci.* 25:3218–3225 (1994).

Hildreth et al., "A Human Lymphocyte–associated Antigen Involved in Cell–mediated Lympholysis" *European Journal of Immunology* 13:202–208 (1983).

Hourmant et al., "A randomized multicenter trial comparing leukocyte function–associated antigen–1 monoclonal antibody with rabbit antithymocyte globulin as induction treatment in first kidney transplantations" *Transplantation* 62(11):1565–1570 (Dec. 15, 1996).

Hourmant et al., "Administration of an Anti–CD11a Monoclonal Antibody in Recipients of Kidney Transplantation" *Transplantation* 58(3):377–380 (Aug. 1994).

Isaacs et al., "Humanized anti–CD4 monoclonal antibody therapy of autoimmune and inflammatory disease" *Clinical & Experimental Immunology* 110(2):158–166 (Nov. 1997).

Isobe et al., "Specific acceptance of cardiac allograft after treatment with antibodies to ICAM–1 and LFA–1" *Science* 255(5048:1125–1127 (Feb. 28, 1992).

Kato et al., "Specific acceptance of fetal bowel allograft in mice after combined treatment with anti–intercellular adhesion molecule–1 and leukocyte function–associated antigen–1 antibodies" *Annals of Surgery* 223(1):94–100 (Jan. 1996).

Krensky et al., "The Functional Significance, Distribution, and Structure of LFA–1, LFA–2, and LFA–3: Cell Surface Antigens Associated with CTL–Target Interactions" *The Journal of Immunology* 131(2):611–616 (Aug. 1983).

Kuypers and Roos, "Leukocyte Membrane Adhesion Proteins LFA–1, CR3 and p150,95: A Review of Functional and Regulatory Aspects" *Res. Immunol.* 140:461–486 (1989).

Le Mauff et al., "Effect of anti–LAF1 (CD11a) monoclonal antibodies in acute rejection in human kidney transplantation" *Transplantation* 52(2):291–296 (Aug. 1991).

Nakakura et al., "Potent and Effective Prolongation by Anti–LFA–1 Monoclonal Antibody Monotherapy of Non–Primarily Vascularized Heart Allograft Survival in Mice Without T Cell Depletion" *Transplantation* 55(2):412–417 (Feb. 1993).

Nishihara et al., "Potent immunosuppressive effect of anti–LFA–1 monoclonal antibody on islet allograft rejection" *Transplantation Proc.* 27:372 (1995).

Nishimura et al., "Lymphokine–activated cell–associated antigen involved in broad–reactive killer cell–mediated cytotoxicity" *Cellular Immunology* 94(1):122–132 (Aug. 1985).

Nishimura et al., "The role of lymphokine–activated cell–associated antigen. III. Inhibition of T–cell activation by monoclonal killer–blocking antibody" *Cellular Immunology* 107(1):32–39 (Jun. 1987).

Raasveld et al., "Complement activation during OKT3 treatment: a possible explanation for respiratory side effects" *Kidney International* 43(5):1140–1149 (May 1993).

Sanchez–Madrid et al., "Mapping of antigenic and functional epitopes on the α–and β–subunits of two related mouse glycoproteins involved in cell interactions, LFA–1 and MAC–1" *Journal of Experimental Medicine* 158(2):586–602 (Aug. 1, 1983).

Springer et al., "The lymphocyte function–associated LFA–1, CD2, and LFA–3 molecules: cell adhesion receptors of the immune system" *Annual Review of Immunology* 5:223–252 (1987).

Stoppa et al., "Anti–LFA1 Monoclonal Antibody (25.3) for Treatment of Steroid–resistant Grade III–IV Acute Graft–versus–host Disease" *Transplant International* 4:3–7 (1991).

Talento et al., "A single administration of LFA–1 antibody confers prolonged allograft survival" *Transplantation* 55:418–422 (1993).

Tanaka et al., "Prolonged inhibition of an antigen–specific IgE response in vivo by monoclonal antibody against lymphocyte function–associated antigen–1" *European Journal of Immunology* 25:1555–1558 (1995).

Taylor et al., "The expression of CD18 is increased on Trisomy 21 (Down syndrome) lymphoblastoid cells" *Clinical & Experimental Immunology* 71(2):324–328 (Feb. 1988).

ten Berge et al., "Consequences of OKT3 administration via continuous infusion as compared to bolus infusion" *Transplantation Proceedings* 28(6):3217–3220 (Dec. 1996).

Van Dijken et al., "Evidence That Anti–LFA–1 in vivo Improves Engraftment and Survival After Allogeneic Bone Marrow Transplantation" *Transplantation* 49(5):882–886 (May 1990).

Vasconcellos et al., "Cytotoxic Lymphocyte Gene Expression in Peripheral Blood Leukocytes Correlates with Rejecting Renal Allografts" *Transplantation* 66:562–566 (1998).

Walker et al., "T Cell Subsets and Their Soluble Products Regulate Eosinophilia in Allergic and Nonallergic Asthma" *J. Immunol.* 146(6):1829–1935 (Mar. 15, 1991).

Ward et al., "Blocking of Adhesion Molecules in vivo as Anti–Inflammatory Therapy" *Therapeutic Immunology* 1:165–171 (994).

Ward et al., "Theophylline—an Immunomodulatory Role In Asthma?" *Am. Rev. Respir. Dis.* 147(3):518–523 (1993).

Werther et al., "Humanization of an Anti–Lymphocyte Function–Associated Antigen (LFA)–1 Monoclonal Antibody and Reengineering of the Humanized Antibody for Binding to Rhesus LFA–1" *J. of Immunology* 157:4986–4995 (1996).

Woodle et al., "OKT3 escalating dose regimens provide effective therapy for renal allograft rejection" *Clinical Transplantation* 10(4):389–395 (Aug. 1996).

* cited by examiner

| Group | Dose (mg/kg) | n | Day 0 | Day 28 | Day 56 |
|---|---|---|---|---|---|
| A | 0.1/qow | 4 | 23.6 ± 8.1 | -11.3 ± 15.1 | -4.6 ± 5.6 |
| B | 0.1 | 6 | 21.2 ± 6.5 | -8.2 ± 15.1 | -14.1 ± 17.0 |
| C | 0.3* | 17 | 25.6 ± 7.4 | -24.5 ± 21.7 | -40.4 ± 28.1 |
| D | 0.3-0.6 | 6 | 23.8 ± 4.5 | -30.1 ± 13.7 | -39.6 ± 28.9 |
| E | 0.3-1.0 | 6 | 28.1 ± 6.1 | -38.6 ± 16.7 | -45.4 ± 31.2 |
| Total | | 39 | 24.8 ± 6.8 | -23.7 ± 20.0 | -33.2 ± 28.4 |

Figure 2

| hu1124 Dose Groups (combined) | Dose (mg/kg) | % Decrease in PASI Score Mean (±S.D) |
|---|---|---|
| A+B | 0.1 | 10.3 (± 13.9) |
| C+D+E | ≥ 0.3 | 41.3 (± 27.9) |
| p value | | .0019 |

Figure 3

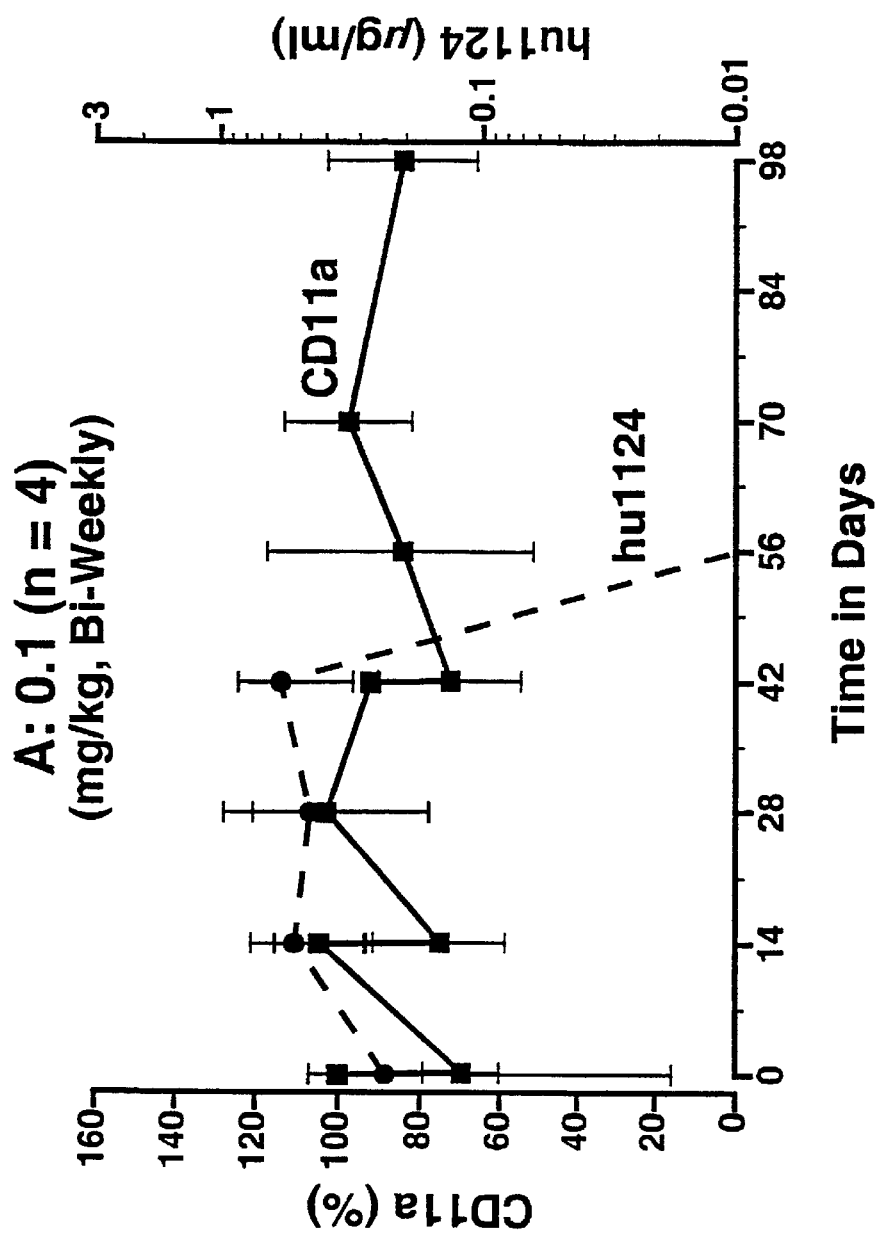
Figure 4-A

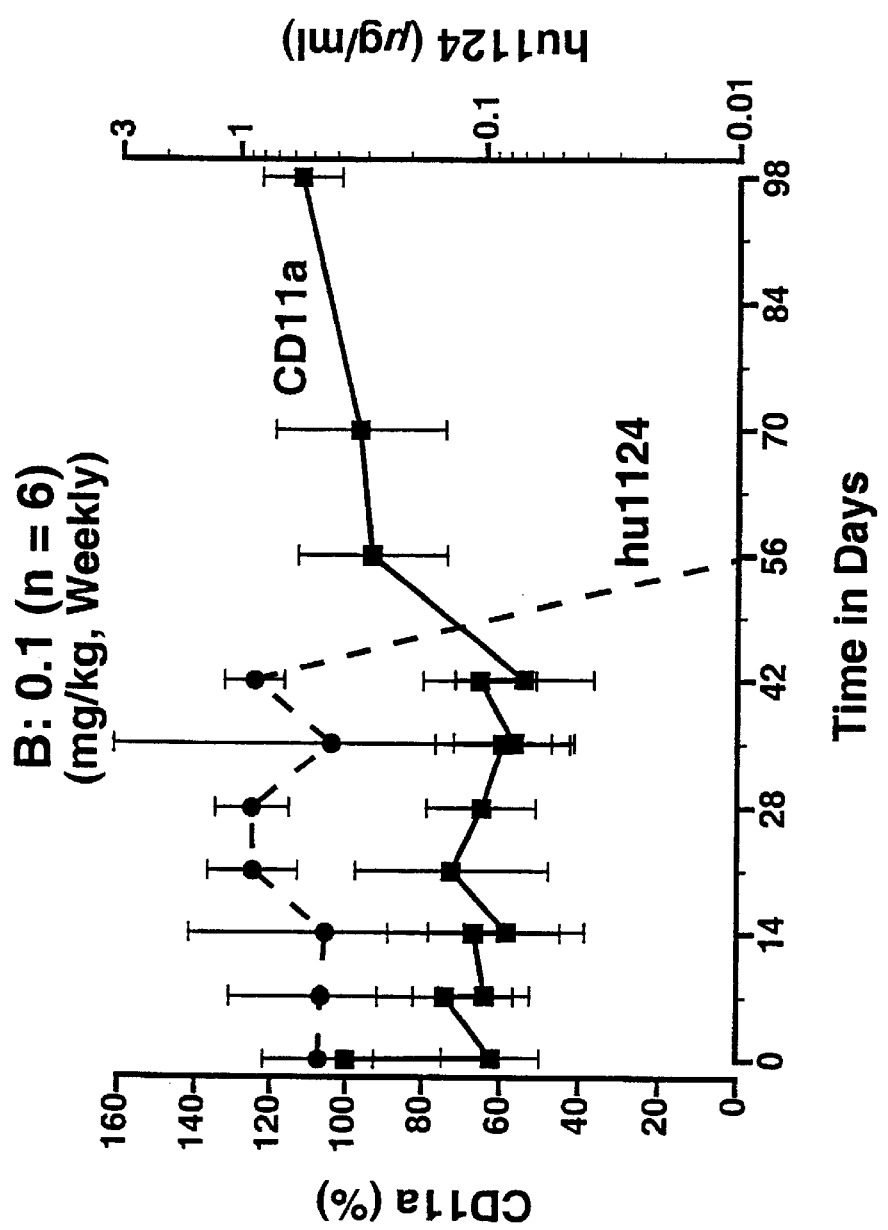
Figure 4-B

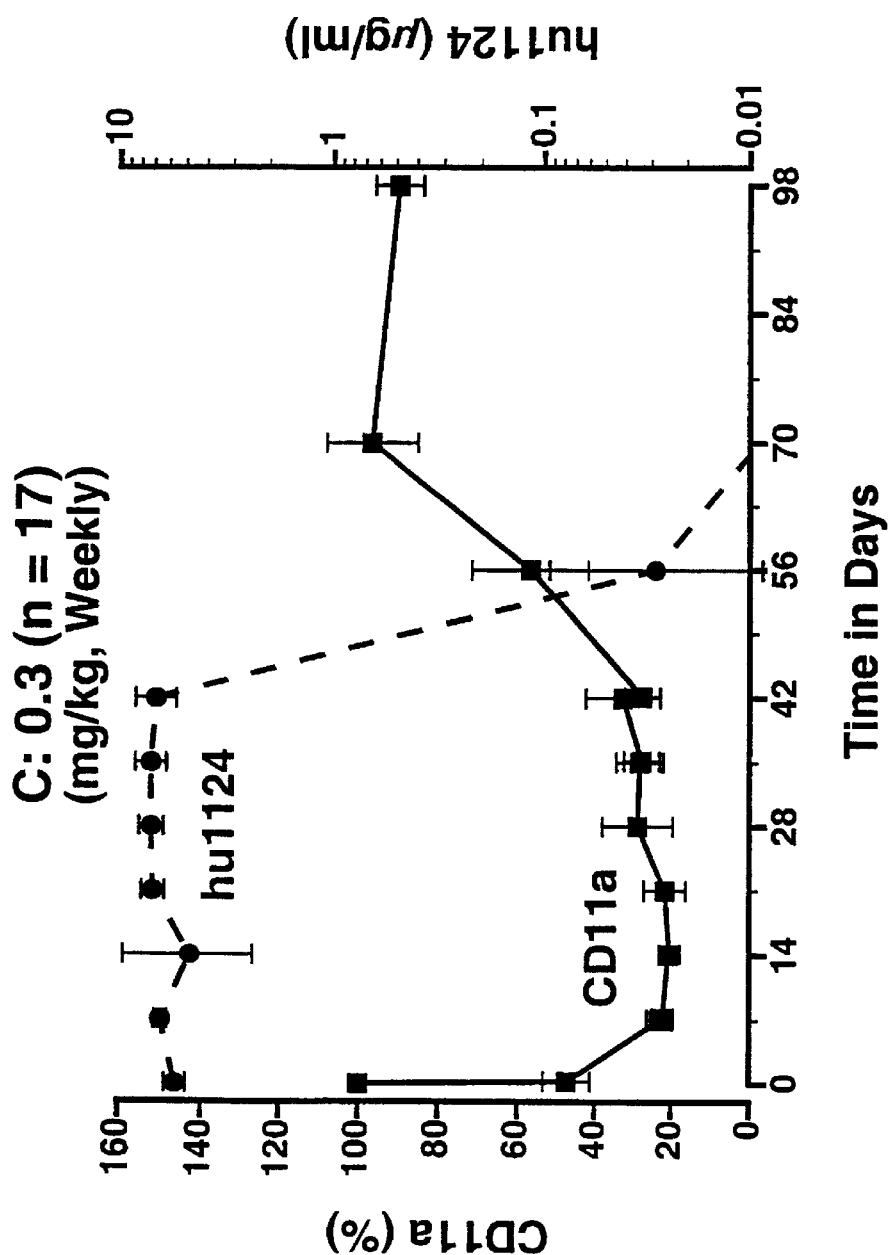
Figure 4-C

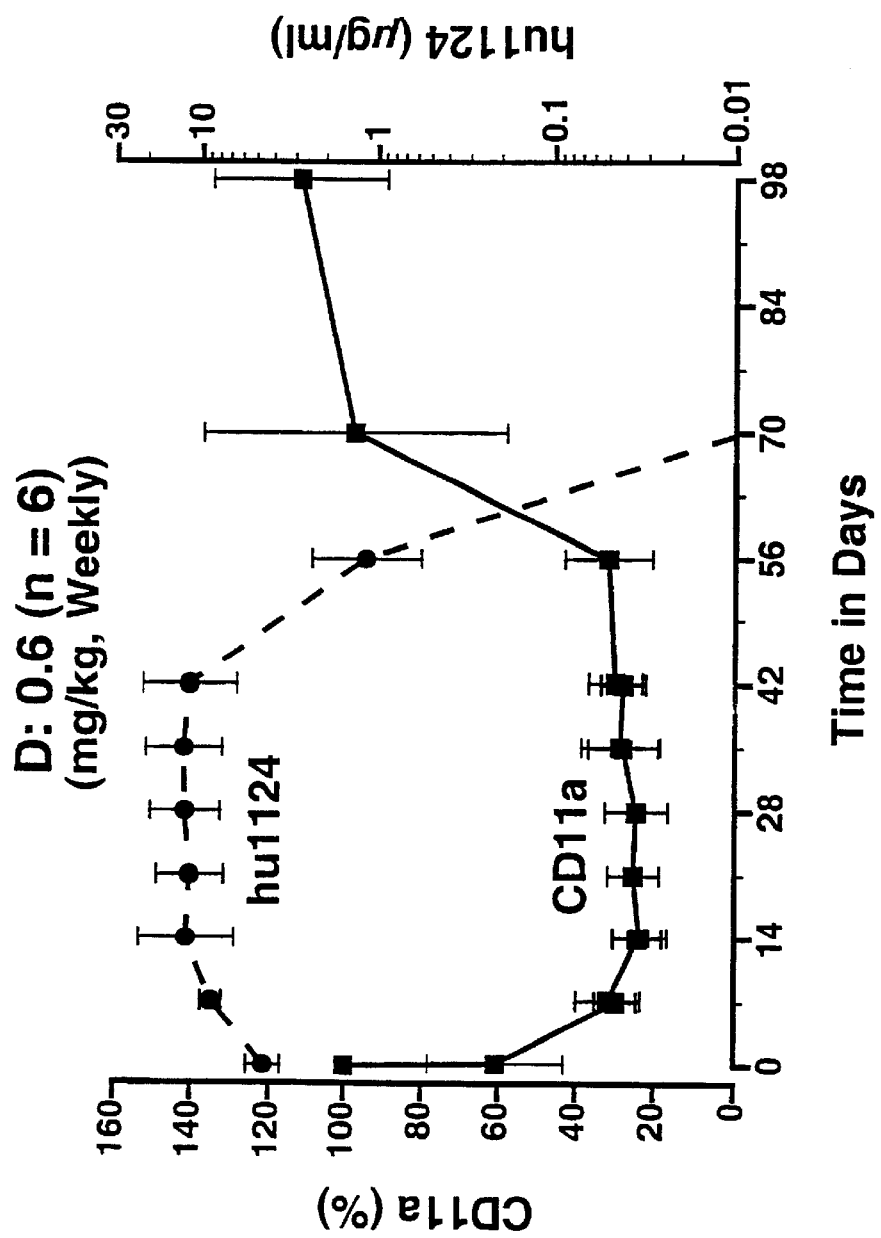
Figure 4-D

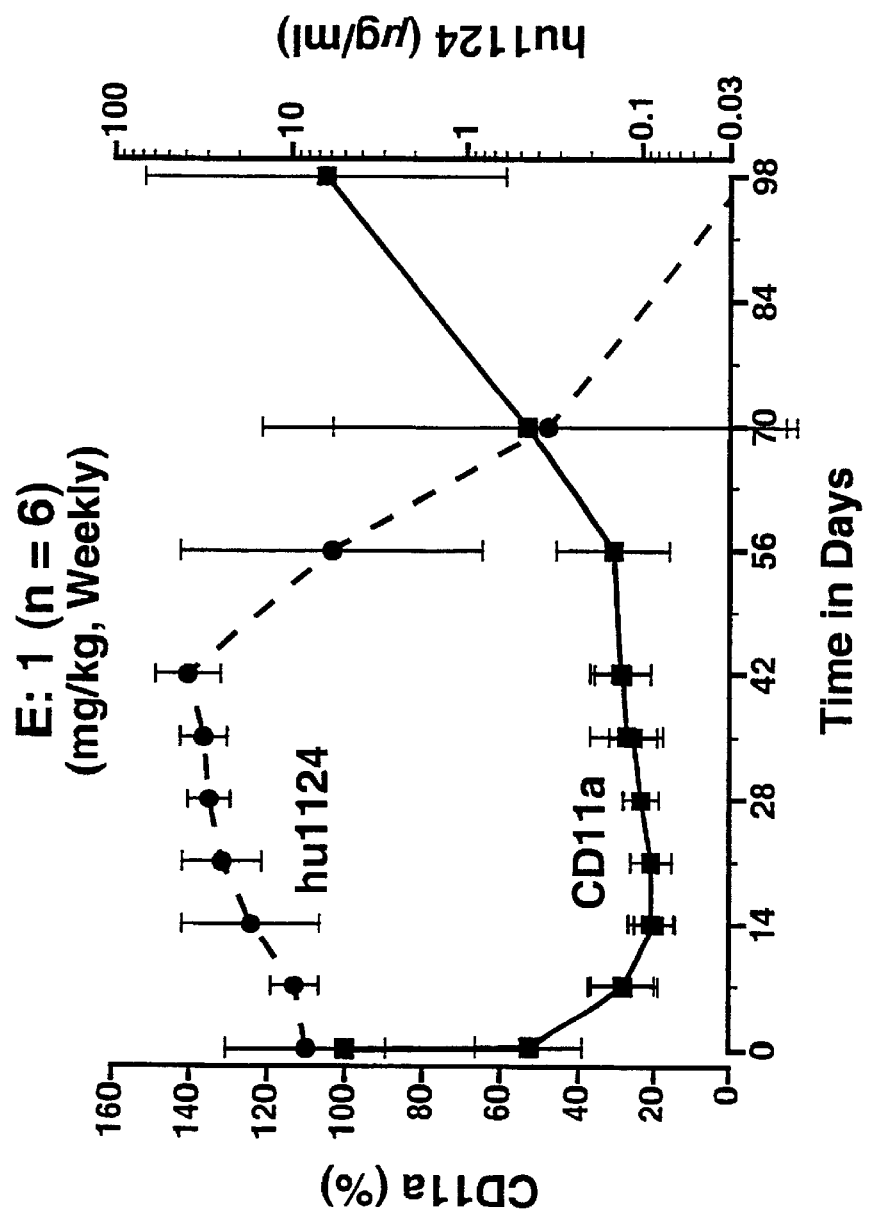
Figure 4-E

Day 56

| Group | Dose (mg/kg) | # of Patients with Decreased Staining | | |
|---|---|---|---|---|
| | | ICAM-1 | Ker 16 | CD11a |
| A | 0.1/qow | 0/4 | 0/4 | 0/4 |
| B | 0.1 | 1/4 | 1/4 | 2/4 |
| C | 0.3 | 8/12 | 8/12 | 12/12 |
| D | 0.3-0.6 | 3/6 | 5/5 | 4/5 |
| E | 0.3-1.0 | 3/4 | 4/4 | 4/4 |

Figure 5

| Group | Dose (mg/kg) | Study Day | | | | | | | |
|---|---|---|---|---|---|---|---|---|---|
| | | 0 | 7 | 14 | 21 | 28 | 35 | 42 |
| A | 0.1/qow | | | | | | | |
| B | 0.1 | | 1 | | | | | |
| C | 0.3 | 14 | 3 | 1 | 2 | 4 | 2 | 2 |
| D | 0.3-0.6 | 8 | | 1 | | 1 | | |
| E | 0.3-1.0 | 5 | | 1 | | | | 1 |
| Total | | 27 | 4 | 3 | 2 | 5 | 2 | 3 |

Figure 6

TREATMENT OF LFA-1 ASSOCIATED DISORDERS WITH INCREASING DOSES OF LFA-1 ANTAGONIST

This application claims the benefit of Provisional application Ser. Nos. 60/125,228, filed Mar. 19, 1999, 60/125,351, filed Mar. 19, 1999 and 60/273,043, filed Mar. 2, 2001.

FIELD OF THE INVENTION

The invention relates to methods of treating mammals, for example humans, to reduce the occurrence of undesired administration reactions, to treat an LFA-1 mediated disease, to condition a mammal to tolerate high doses of a therapeutic compound and to down modulate a cell surface receptor.

DISCUSSION OF THE BACKGROUND

Admninistration of many therapeutic agents rapidly induces adverse side effects, or events, including but not limited to fever, headache, nausea, vomiting, breathing difficulties and changes in blood pressure. These adverse events limit the amount of a drug or therapeutic compound that can be given, which in turn limits the therapeutic effectiveness that could be achieved with higher doses of the drug. There is a continuing need to develop techniques which limit the toxicity of higher drug doses so that therapeutic efficacy can be improved. This need exists for both polypeptide and non-polypeptide compounds.

Antibodies are one type of polypeptide compound for which there are frequently adverse events upon administration which limit the dose of the compound that can be administered. One compound associated with adverse side effects is the murine monoclonal antibody OKT3. OKT3 binds to the CD3 protein complex that is associated with the T cell receptor (TCR) found on the surface of all T lymphocytes. Administration of OKT3 to humans rapidly reduces the number of circulating T cells (e.g. OKT3 is a cell depleting compound) and reduces the amount of cell surface TCR found on those T cells that remain (Cosimi, et al., 1981 N Engl J Med. 305(6), 308–314). The immunosuppressive effects of OKT3 have been therapeutically useful in the treatment of renal transplant rejection (Goldstein & Group, 1985 M Engl J Med, 313(6), 337–342). However, administration of OKT3 induces a number of adverse side effects, including fever, chills, nausea, vomiting and tightness of chest. These side effects are believed to be caused by cytokine release from T cells due to OKT3-induced activation (Abramowicz et al., 1989 Transplantation. 47(4), 606–608) and complement activation (Raasveld, et al., 1993 Kidney International, 43, 1140–1149).

Several strategies have been developed to reduce the OKT3-induced side effects. Anti-inflammatory steroids have been shown to attenuate the OKT3-induced cytokine release (Goldman, et al., 1989 Lancet, ii (8666), 802) (Chatenoud, et al., 1990 Transplantation, 49(4), 697–702), and indomethacin can reduce the febrile response (First, Schroeder, Hariharan, Alexander, & Weiskittel, 1992 Transplantation. 53(1), 91–94). A standard 5 mg dose of OKT3 administered as a 2 hour infusion instead of the usual bolus injection was better tolerated and reduced complement activation, but not the cytokine release (ten Berge, Buysmann, van Diepen, Surachno, & Hack, 1996 Transplant Proc, 28 (6), 3217–3220). The adverse events induced by OKT3 are most significant after the first dose. While the initial dose (typically 5 mg) induces cytokine release and activates complement it also eliminates the target T cells. With fewer T cells and reduced TCR density on those that do remain, subsequent doses of OKT3 induce less cytokine release (Chatenoud, et al., 1989 N Engl J Med, 320 (21), 1420–1421). One group found that after four daily doses of 5 mg, dosing could safely be escalated to 10, 15, and 25 mg over the next 3 days (Woodle. et al., 1996 Clin Transplantation, 10, 389–395)

Adverse events have also been associated with the initial administration of monoclonal antibodies directed to other cell surface molecules. A humanized anti-CD4 monoclonal antibody induced fever, chills, hypotension and chest tightness when given intravenously to psoriasis and rheumatoid arthritis patients (Isaacs, et al., 1997 Clin Exp Immunol, 110, 158–166). This treatment down-modulated expression of CD4 and caused a reduction in the number of circulating CD4-positive T cells, and but was not completely depleting. Bispecific antibodies that interact with the CD64 molecule, a receptor for the constant region of immunoglobulin (Fc gamma RI), and tumor associated molecules (epidermal growth factor receptor MDX-447, or HER2/neu MDX-H210) were shown to cause flu-like symptoms such as fever and chills after the first dose (Curnow, 1997, Cancer Immunol Immunother, 45, 210–215). Similar to the effect of OKT3 on T cells, these antibodies caused a decrease in the number of circulating monocytes, which express CD64, and stimulated increases in plasma cytokines. A single dose of another monoclonal antibody directed to CD64 (MDX-33) down-modulated the expression of CD64 on monocytes and also caused chills, low-grade fever, headache and muscle aches.

The interaction of T-lymphocytes with antigen-presenting cells (APCs) is one of the initial steps in the activation of an immunological response to what is perceived by the immune system to be a foreign antigen. Although much attention has been focused on the primary interaction of the T-cell receptor with the MHC-antigen on the APC, several other cell surface components are also involved in T-cell activation. These ligand pairs located on the cell surface of the T-cell and the APC include: LFA-1/ICAM-1 (also ICAM-2 and ICAM-3), CD28/B7, CD2/LFA-3, CD4/MHC Class II, and CD8/MHC Class I. Interfering with the of any of these ligand pairs (e.g., with the use of binding molecules such as monoclonal antibodies) may decrease, inhibit, or discontinue the T-cell responses (de Fourgerolles et al., 1994, J. Exp. Med., 179:619–29; Dustin, M L et al, 1986, J Immunol, 137:245–54).

LFA-1 (consisting of CD11a and CD18 subunits) interaction with ICAM is necessary for T-cell killing, T-helper and B-cell responses, natural killing, and antibody-dependent cytotoxicity. In addition, LFA-1/ICAM interactions are involved in adherence of leukocytes to endothelial cells, fibroblasts, and epithelial cells, facilitating the migration of leukocytes from the vasculature to the sites of inflammation (Collins, T., 1995, Science and Medicine, 28–37; Dustin, ML. et al., 1991, Annual Rev Immunology, 9:27–66).

Using antibodies that interfere with LFA-1/ICAM interactions decreases or inhibits the inflammatory process by blocking the activation of T-cells and/or the extravasation of leukocytes. In vitro, monoclonal antibodies against LFA-1 or its ligands have inhibited T-cell activation (Kuypers, T. and Roos, D., 1989, Research in Immunology, 140:461–86; Springer, T A, 1987, Annual Rev Immunology, 5:223–52), T-cell dependent B-cell proliferation (Fischer, A. et al., 1986, J Immunol, 136:3198–203), target cell lysis (Krensky, A. et al., 1983, J Immunol, 131:6711–6), and adhesion of T-cells to vascular endothelium (Dustin, M L. et al., 1988, Journal of Cell Biology, 107:321–31). In mice, anti-CD11a antibodies have induced tolerance to protein antigens (Benjamin, R. et al, 1988, European Journal of Immunology, 18:1079–88; Tanaka, Y. et al., 1995, European Journal of Immunology, 25:1555–8), delayed the onset and reduced the severity of experimental autoimmune encephalomyelitis (Gordon, EJ et al., 1995, Journal of Neuroimmunology, 62:153–60), inhibited lupus-associated autoantibody production, and prolonged survival of several types of tissue grafts (Cavazzana-Calco M S, Sarnacki S, Haddad E, et al., Transplantation 1995;59(11):1 576–82; Nakakura E K, McCabe S M, Zheng B, Shorthouse R A, et al., Transplantation 1993;55(2):412–7; Connolly M K, Kitchens E A, Chan B, et al, Clinical Immunology and lmmunopathology 1994;72(2):198–203; He Y, Mellon J, Apte R, Niederkorn J., Investigative Ophthalmology and Visual Science 1994;35(8):3218–25; Isobe M. Yagita H, Okumura K, Ihara A., Science 1992;255:1125–7; Kato Y, Yamataka A, Yagita H, et al., Ann Surg 1996;223(1):94–100; Nishihara M, Gotoh M, Fukuzaki T, et al., Transplantation Proceedings 1995;27(1):372; Talento A, Nguyen M, Blake T, et al, Transplantation 1993;55(2):418–22; van Dijken P J, Ghayur T, Mauch P, et al., Transplantation 1990;49(5):882–6). In human clinical studies, murine anti-CD11a monoclonal antibodies have been shown to help prevent graft failure following bone marrow transplantation (Cavazzana-Calco M S, Bordigoni P, Michel G, et al., British Journal of Haematology 1996;93:131–8; Fischer A, Friedrich W, Fasth A., Blood 1991;77(2):249–56; Stoppa A M, Maraninchi D, Blaise D, Viens P, et al., Transplant International 1991;4:3–7) and renal transplantation (Hounnant M, Le Mauff B, Le Meur Y, et al., Transplantation 1994;58(3):377–80; Hourrnant M, Bedrossian J, Durand D, et al., Transplantation 1996;62(11):1565–70; Le Mauff B, Hourmant M, Rougier J P, et al., Transplantation 1991;52(2):291 6). An immunosuppressive drug that could reduce the incidence of both acute graft rejection and delayed graft function, while promoting long-term survival with minimum toxicity with the potential of tolerance induction would provide major benefits to the field of renal transplantation.

A need continues to exist for new methods of administering therapeutic compounds which reduces side effects and which increases the effectiveness of the therapeutic compound.

SUMMARY OF THE INVENTION

One object of the present invention is to provide an improved method of administering a therapeutic compound. This and other objects which will become apparent from the following description of enabling embodiments have been achieved by the method of the invention.

One aspect of the invention is a method for reducing the occurrence of fever, headache, nausea and/or vomiting associated with administration of a therapeutic compound to a mammal in need thereof by administering to the mammal a first conditioning dose of a non-target cell depleting compound which binds to a cell surface receptor on a target mammalian cell; and then administering at least a second therapeutic dose of the compound, wherein the second dose is higher than the first dose.

A further aspect of the invention is a method for treating an LFA-1 mediated disorder by administering to a mammal in need thereof a first conditioning dose of a compound which binds to lymphocyte surface receptor LFA-1; and then administering at least a second therapeutic dose of the compound, wherein the second dose is higher than the first dose. LFA-1 mediated disorders contemplated include psoriasis, asthma, rheumatoid arthritis, multiple sclerosis and transplant rejection. In a specific embodiment, the graft or transplant is a renal transplant.

A further aspect of the invention is a method for conditioning a mammal to tolerate high doses of a therapeutic compound by administering to the mammal a first conditioning dose of a non-target cell depleting compound which binds to a cell surface receptor on a target mammalian cell; and then administering at least a second therapeutic dose of the compound, wherein the second dose is higher than the first dose.

Another aspect of the invention is a method for down modulating a cell surface receptor in a mammalian cell population by contacting a target mammalian cell displaying a receptor molecule on the surface thereof with a first dose of a ligand which binds to the receptor molecule and does not deplete the mammalian cell population; and then further contacting the mammalian cell population with at least a second dose of the ligand, wherein the second dose is higher than the first dose.

The following preferred embodiments apply to all the above methods of the invention. In preferred embodiments, the therapeutic compound comprises a polypeptide which binds to an extracellular domain of the receptor molecule. A preferred polypeptide is an antibody or a fragment thereof. In one embodiment, the target mammalian cell is a lymphocyte such as a T lymphocyte. Non-T cell-depleting compounds or antibodies that bind CD11a or CD18 cell surface receptors on a T cell, including the humanized anti-CD11a antibody hu1124, are specifically encompassed.

Intravenous or subcutaneous mode of administration of the therapeutic compound is contemplated. In a specific embodiment, administration is not more than once per week. In an additional embodiment of each of the above methods, the methods further comprise administering a third therapeutic dose, wherein the third dose is higher than the second dose. Yet a further embodiment is the administration of a fourth therapeutic dose, wherein the fourth dose is higher than or equal to the third dose.

Also provided is composition comprising an anti-CD11a antibody or fragment thereof, and a pharmaceutical carrier, for use as an active pharmaceutical agent for treating an LFA-1 mediated disorder, wherein the antibody is a non-target cell-epleting antibody and wherein the composition is administered to the mammal as a first conditioning dose followed by a second therapeutic dose, wherein the second therapeutic dose is higher than the first dose. Another aspect is the use of a compound which binds to the lymphocyte surface receptor LFA-1 in the preparation of a medicament for the treatment of an LFA-1 mediated disorder, which treatment comprises administering to the mammal, a first conditioning dose of the compound followed by a second therapeutic dose of the compound wherein the second therapeutic dose is higher than the first dose.

Other aspects of the invention will become apparent from the following description of preferred embodiments which are not intended to be limiting of the invention.

BRIEF DESCRIPTION OF THE FIGURES

FIG. 2 shows the changes in PASI score results by dose group for the study of Example 1. It is a summary of Mean Percent Change (+/−SD) in PASI scores from baseline to Days 28 and 56. *Subject 015 withdrew consent at Day 7 and did not have any data for Days 28 and 56.

FIG. 3 shows the dose response reduction in PASI score results for the study of Example 1.

FIG. 4 shows the modulation of lymphocyte CD11a and plasma hu1124 levels for each of Groups A–E, for the study of Example 1.

FIG. 5 summarizes histologic data from Example 1. Histologic evidence of decreased ICAM-1, Keratin 16 (Ker 16), and CD11a expression in psoriatic plaques is shown.

FIG. 6 shows the decrease in acute adverse events over time, achieved in Example 1 using the method of the invention. An acute adverse event is one or more of fever (mild), headache (mild), nausea or vomiting within 24 hours of dosing. A single patient may have had more than one event.

DEFINITIONS

Figure 1:
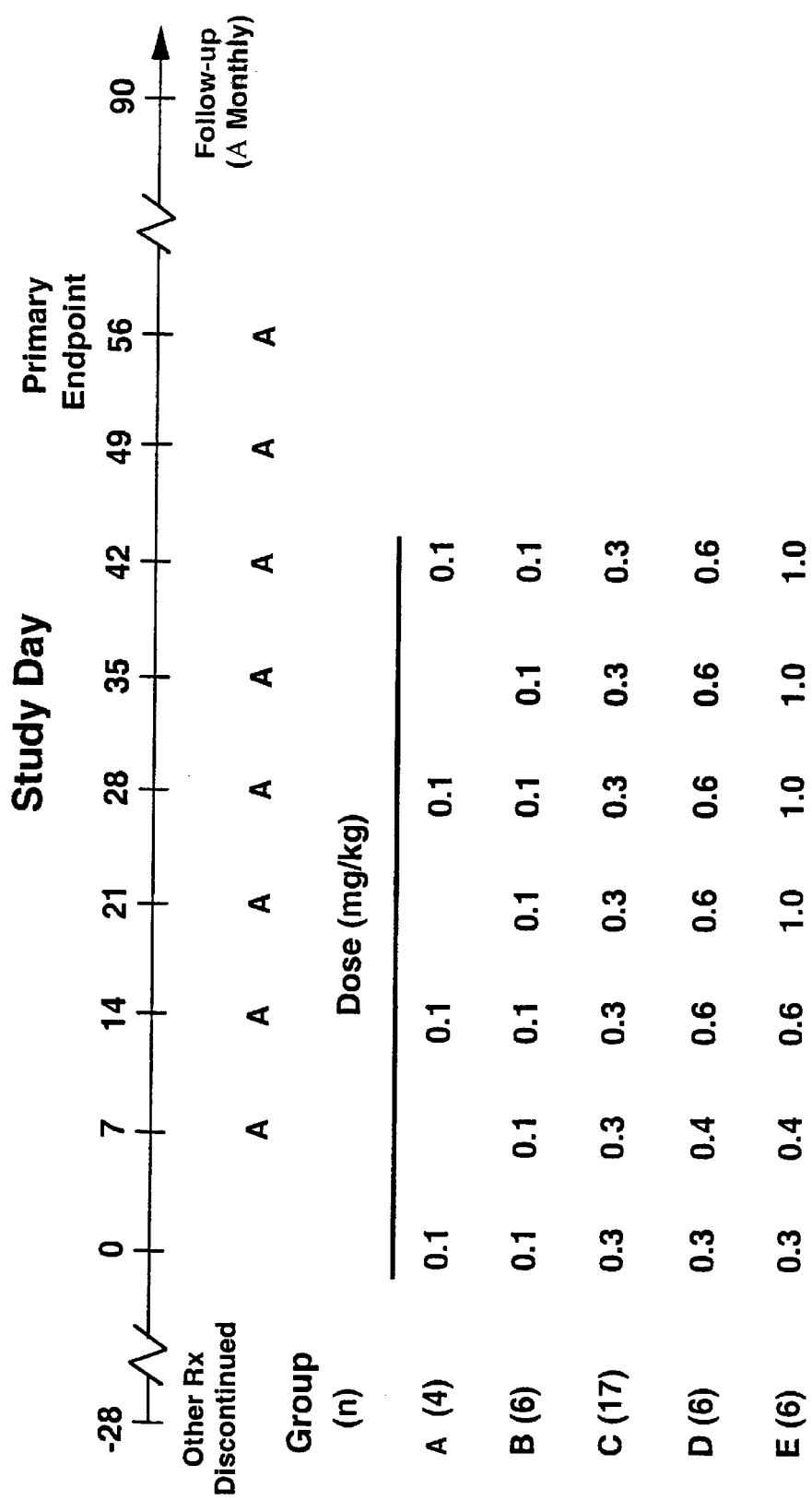
FIG. 1 shows the dosing schedule used in the study of Example 1. A indicates time of Physician's Global Assessment and PASI, and skin biopsy.

The term "antibody" is used in the broadest sense and specifically covers single monoclonal antibodies, antibody compositions with polyepitopic specificity, as well as antibody fragments (e.g., Fab, F(ab')$_2$, scFv and Fv), so long as they exhibit the desired biological activity. The term "monoclonal antibody" as used herein refers to an antibody obtained from a population of substantially homogeneous antibodies, ie., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature*, 256:495 (1975), or may be made by recombinant DNA methods (see, e.g., U.S. Pat. No. 4,816,567 (Cabilly et al.)).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity, e.g. binding to a cell surface receptor (U.S. Pat. No. 4,816,567 (Cabilly et al.); and Morrison et al., *Proc. Natl. Acad Sci. USA*, 81:6851–6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature*, 321:522–525 (1986); Reichmann et al., *Nature*, 332:323–329 (1988); and Presta, *Curr. Op. Struct. Biol.*, 2:593–596 (1992)

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Nail. Acad. Sci. USA* 90:6444–6448 (1993).

The expression "linear antibodies" when used throughout this application refers to the antibodies described in Zapata ei al. *Protein Eng.* 8(10): 1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

A "variant" antibody, refers herein to a molecule which differs in amino acid sequence from a "parent" antibody amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind the receptor and preferably has properties which are superior to those of the parent antibody. For example, the variant may have a stronger binding affinity, enhanced ability to activate the receptor, etc. To analyze such properties, one should compare a Fab form of the variant to a Fab form of the parent antibody or a full length form of the variant to a full length,form of the parent antibody, for example, since it has been found that the format of the antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody.

The term "down modulating a cell surface receptor" means a process or method which reduces the number of molecules of the receptor on the surface of a cell type relative to the number of molecules of the receptor before the process or method was performed. For example, the administration of a therapeutic compound which binds to a cell surface receptor will down regulate the receptor if the number of receptor molecules on the surface of the cell is less after administration than before administration of the compound. The number of cell surface receptor molecules can be measured histologically using known staining and counting methods.

A "conditioning dose" is a dose which attenuates or reduces the frequency or the severity of first dose adverse side effects associated with administration of a therapeutic compound. The conditioning dose may be a therapeutic dose, a sub-therapeutic dose, a symptomatic dose or a sub-symptomatic dose. A therapeutic dose is a dose which exhibits a therapeutic effect on the patient and a sub-therapeutic dose is a dose which does not exhibit a therapeutic effect on the patient treated. A symptomatic dose is a dose which induces at least one adverse effect on administration and a sub-symptomatic dose is a dose which does not induce an adverse effect.

The term "cell surface receptor" as used herein means any molecule displayed on the surface of a cell and available for binding by therapeutic compounds which contact the surface of the cell. Such a cell surface molecule is a "receptor" for the therapeutic compound. Human leukocyte surface markers, including but not limited to CD2, CD29, CD40, CD49a–d and CD58 may be cell surface receptors within the invention. Suitable cell surface receptors also include cell adhesion molecules such as the leukocyte integrins CD11a/CD18, CD11b/CD18, CD11c/CD18 and CD11d/CD18 which are heterodimeric surface receptor molecules. A therapeutic compound may bind to either member of the heterodimeric pair. The cell surface receptor may have an extracellular domain which available for binding to a therapeutic compound as well as transmembrane and intracellular domains. Other examples of receptors include protein kinase receptors capable of intracellular signaling through tyrosine phosphorylation, etc.

The term "non-target cell depleting compound" or a compound or ligand which "does not deplete" a cell population means a compound which binds to a cell surface receptor molecule, but does not substantially reduce the number of cells in the cell population. A non-depleting compound, for example, will reduce the number of cells in a cell population by about 50% or less, preferably by about 30% or less, more preferably by about 20% or less, relative to the number of target cells in the cell population prior to contact or treatment with the compound.

The term "LFA-1-mediated disorders" refers to pathological states caused by cell adherence interactions involving the LFA-1 receptor on lymphocytes. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitic; allergic conditions such as eczema and asthma and other conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; diseases involving leukocyte diapedesis; CNS inflammatory disorder, multiple organ injury syndrome secondary to septicaemia or trauma; autoimmune haemolytic anemia; myethemia gravis; antigen-antibody complex mediated diseases; all types of transplantation rejection, including graft vs. host or host vs. graft disease; etc.

"Treating" a disease, disorder, condition or cell population includes therapy and prophylactic treatment on an acute short term basis and on a chronic long-term basis.

The term "mammal" refers to any animal classified as a mammal, including humans, domestic and farm animals, and zoo, sports, or pet animals, such as dogs, horses, cats, cows, etc. Preferably, the mammal herein is human.

A "ligand" or a "compound" which binds to a receptor molecule on the surface of a cell may be any compound capable of binding to the receptor molecule. The therapeutic compound may, for example, be a small organic molecule (preferably having a molecular weight of about 1000 g/mole or less) or a polypeptide. Suitable polypeptide compounds or ligands can be prepared by methods known in the art, for example, by isolating peptides or proteins having high binding affinities for the surface molecule using phage display technology. Phage display methods are disclosed, for example, in U.S. Pat. No. 5,750,373; U.S. Pat. No. 5,821,047; U.S. Pat. No. 5,780,279; U.S. Pat. No. 5,403,484; U.S. Pat. No. 5,223,409; U.S. Pat. No. 5,571,698; etc. In these methods, large libraries of peptides or proteins displayed on the surface of phage are produced and screened or panned to select those members of the library which bind strongly to a target molecule which is generally immobilized on a solid support. These methods may be used to select peptides or proteins which bind to a cell surface receptor by screening a phage display library using the cell surface receptor as the target molecule. Repeated rounds of selection and separation of the binders having high binding affinity produces polypeptide compounds capable of binding to the cell surface receptor. The polypeptide may be an antibody or an antibody fragment.

A "therapeutic" compound is any compound which is used in treating a mammal.

The term "a compound which binds to lymphocyte surface receptor LFA-1" generally refers to any compound capable of binding to either component of LFA-1. The compound may be a protein which recognizes and binds to LFA-1, for example a binding protein, an antibody directed against either CD11a or CD18 or both, but also includes ICAM-1, soluble forms of ICAM-1 (e.g., the ICAM-1 extracellular domain, alone or fused to an immunoglobulin sequence), antibodies to ICAM-1, and fragments thereof, or other molecules capable of inhibiting the interaction of LFA-1 and ICAM-1.

The term "anti-LFA-1 antibody" or "anti-LFA-1 MAb" refers to an antibody directed against either CD11a or CD18 or both. The anti-CD11a antibodies include, e.g., MHM24 [Hildreth et al., Eur. J. Immunol., 13: 202–208 (1983)], R3.1 (IgG1) [R. Rothlein, Boehringer Ingelheim Pharmaceuticals, Inc., Ridgefield, Conn.], 25-3 (or 25.3), an IgG1 available from Immunotech, France [Olive et al., in Feldmann, ed., Human T cell Clones. A new Antroach to Immune Regulation, Clifton, N.J., Humana, 1986 p. 173], KBA (IgG2a) [Nishimura et al., Cell. Immunol., 107: 32 (1987); Nishimura et al., ibid, 94: 122 (1985)], M7/15 (IgG2b) [Springer et al., Immunol. Rev., 68: 171 (1982)], IOT16 [Vermot Desroches et al., Scand. J. Immunol., 33: 277–286 (1991)], SPVL7 [Vermot Desroches et al., supra], and M17 (IgG2a), vailable from ATCC, which are rat anti-murine CD11a antibodies. Preferred anti-CD11a antibodies are the humanized antibodies described in WO 98/23761.

Examples of anti-CD18 antibodies include MHM23 [Hildreth et al., supra], M18/2 (IgG2a) [Sanches-Madrid et al., J. Ext. Med., 158: 586 (1983)], H52 [Fekete et al., J. Clin. Lab Immunol., 31: 145–149 (1990)], Mas191c [Vermot Desroches et al., supra], IOT18 [Vermot Desroches et al., supra], 60.3 [Taylor et al., Clin. Exp. Immunol., 71: 324–328 (1988)], and 60.1 [Campana et al., Eur. J. Immunol., 16: 537–542 (1986)].

Other examples of suitable LFA-1 binding molecules, including antibodies, are described in Hutchings et al., supra, WO 91/18011 published Nov. 28, 1991, WO 91/16928 published Nov. 14, 1991, WO 91/16927 published Nov. 14, 1991, Can. Pat. Appln. 2,008,368 published Jun. 13, 1991, WO 90/15076 published Dec. 13, 1990, WO 90/10652 published Sept. 20, 1990, EP 387,668 published Sept. 19, 1990, EP 379,904 published Aug. 01, 1990, EP 346,078 published Dec. 13, 1989, U.S. Pat. No. 5,071,964, U.S. Pat. No. 5,002,869, Australian Pat. Appln. 8815518 published Nov. 10, 1988, EP 289,949 published Nov. 9, 1988, and EP 303,692 published Feb. 22, 1989.

The antibody is appropriately from any source, including chicken and mammalian such as rodent, goat, primate, and human. Preferably, the antibody is from the same species as the species to be treated, and more preferably the antibody is human or humanized and the host is human. While the antibody can be a polyclonal or monoclonal antibody, preferably it is a monoclonal antibody, which can be prepared by conventional technology. The antibody is an IgG-1, -2, -3, or 4, IgE, IgA, IgM, IgD, or an intraclass chimera in which Fv or a CDR from one class is substituted into another class. The antibody may have an Fc domain capable of an effector function or may not be capable of binding complement or participating in ADCC.

DETAILED DESCRIPTION OF THE PREFERRED EMBODIMENTS

It has now been discovered that a dosing schedule in which a first conditioning dose of a non-target cell depleting compound which binds to a cell surface receptor on a target mammalian cell is followed by a second higher dose of the compound, is effective in conditioning a mammal to tolerate increasing or higher doses of the therapeutic compound. This dosing schedule allows one to reduce the occurrence of adverse effects which arise from the initial administration and subsequent administrations of the therapeutic compound, that is, the method of the invention reduces the first dose adverse effects of administration and condition the mammal to further higher doses. Although some adverse effects such as fever, headache, nausea, vomiting, breathing difficulties, myalgia, chills and changes in blood pressure will still be observed, the frequency and/or severity of these adverse effects is surprisingly reduced relative to administration using conventional dosing schedules such as daily administration of equal doses of a therapeutic compound. The method of the present invention, therefore, allows one to increase subsequent doses and obtain the therapeutic benefit of higher doses of the therapeutic compounds, while, at the same time, minimizing the occurrence of adverse side effects.

The therapeutic compound which is administered using the dosing schedule of the present invention is a non-target cell depleting compound which binds to a cell surface receptor on the target cell. Such a compound does not substantially reduce the number of cells in the cell population. For example, if the target cell is a lymphocyte, administration of a non-lymphocyte cell depleting compound according to the dosing schedule of the present invention will result in binding of the compound to a lymphocyte cell surface receptor, but will not result in a decrease in the number of circulating lymphocytes over the course of administration of the therapeutic compound. It is contemplated that administration of the therapeutic compound will, in some cases, result in increases in the number of target cells in the cell population, however, and such an effect is to be considered within the scope of the present invention.

The non-target cell depleting compound which is administered according to the method of the invention may be any non-depleting therapeutic compound which is capable of binding to a cell surface receptor. Many therapeutic compounds are well known to exert a therapeutic effect by binding to a selective cell surface marker or receptor. These known therapeutic compounds will be apparent to one having ordinary skill in the art and may be used in the method of the present invention. Suitable therapeutic compounds include non-peptide organic compounds, preferably having a molecular weight less than about 1,000 g/mol, more preferably less than about 600 g/mol; peptide therapeutic compounds, generally containing 8 to about 200, preferably about 15 to about 150, more preferably about 20 to about 100 amino acid residues; and protein therapeutic compounds, generally having secondary, tertiary and possibly quaternary structure. Suitable peptides compounds can be prepared by known solid-phase synthesis or recombinant DNA technology which are well known in the art.

A particularly preferred method of selecting a non-depleting peptide compound is through the use of phage display technology. Using known phage display methods, libraries of peptides or proteins are prepared in which one or more copies of individual peptides or proteins are displayed on the surface of a bacteriophage particle. DNA encoding the particular peptide or protein is within the phage particle. The surface-displayed peptides or proteins are available for interaction and binding to target molecules which are generally immobilized on a solid support such as a 96-well plate or chromatography column support material. Binding and/or interaction of the display peptide or protein with a target molecule under selected screening conditions allows one to select members of the library which bind or react with the target molecule under the selected conditions. For example, peptides which bind under particular pH or ionic conditions may be selected. Alternatively, a target cell population can be immobilized on a solid surface using known techniques and the peptide or protein phage library can be panned against the immobilized cells to select peptides or proteins which bind to cell surface receptors on the target cell population. Phage display techniques are disclosed, for example, in U.S. Pat. No. 5,750,373; U.S. Pat. No. 5,821,047; U.S. Pat. No. 5,780,279; U.S. Pat. No. 5,403,484; U.S. Pat. No. 5,223,407; U.S. Pat. No. 5,571,698; and others.

One category of preferred polypeptide non-depleting compounds, are compounds containing an antibody or a fragment thereof which immunologically recognize and bind to cell surface receptors. Methods of preparing antibodies to specific cell surface receptors are well known in the art and have been practiced for many years. Suitable antibodies may be prepared using conventional hybridoma technology or by recombinant DNA methods. Preferred antibodies are humanized forms of non-human antibodies. Alternatively, antibodies may be prepared from antibody phage libraries using methods described, for example, in U.S. Pat. No. 5,565,332; U.S. Pat. No. 5,837,242; U.S. Pat. No. 5,858,657; U.S. Pat. No. 5,871,907; U.S. Pat. No. 5,872,215; U.S. Pat. No. 5,733,743, and others. Suitable compounds include full-length antibodies as well as antibody fragments such as Fv, Fab, Fab' and F(ab')$_2$ fragments which can be prepared by reformatting the full length antibodies using known methods.

Additional preferred polypeptide therapeutic compounds are immunoadhesin molecules also known as hybrid immunoglobulins. These polypeptides are useful as cell adhesion molecules and ligands and also useful in therapeutic or diagnostic compositions and methods. An immunoadhesin typically contains an amino acid sequence of a ligand binding partner protein fused at its C-terminus to the N-terminus of an immunoglobulin constant region sequence. A suitable immunoadhesin may contain the extracellular domain of a leukocyte integrin molecule, e.g. LFA-1, LFA-2, LFA-3, MAC-1, p150,95, aDb2, etc., fused to the hinge and CH2 and/or CH3 sequences of the a human IgG constant region. lmmunoadhesins and methods of preparing the same are described in U.S. Pat. No. 5,428,130; U.S. Pat. No. 5,714,147; U.S. Pat. No. 4,428,130; U.S. Pat. No. 5,225,538: U.S. Pat. No. 5,116,964; U.S. Pat. No. 5,098,833; U.S. Pat. No. 5,336,603; U.S. Pat. No. 5,565,335; etc.

In a method of the invention, adverse side effects are reduced by administering to a mammal a first conditioning dose of a non-target cell-depleting compound which binds to a cell surface receptor on a target mammalian cell followed by a therapeutic dose. The term "therapeutic" in this context means that the compounds binds to the surface of the target cell and produce a change in the symptoms or conditions associated with the disease or condition which is being treated. It is sufficient that a therapeutic dose produce an incremental change in the symptoms or conditions associated with the disease; a cure or complete remission of symptoms is not required. One having ordinary skill in this art can easily determine whether a dose is therapeutic by establishing criteria for measuring changes in symptoms or conditions of the disease being treated and then monitoring changes in these criteria according to known methods. External physical conditions, histologic examination of affected tissues in patients or the presence or absence of specific cells or compounds, including in a lesion, associated with a disease may provide objective criteria for evaluating therapeutic effect. In one example, the method of the invention may be used to treat psoriasis where therapeutic effect is determined by a physician's global assessment (PGA) of the patient and by Psoriases Area and Severity Index (PASI) scores. A decrease in PASI score indicates a therapeutic effect. Psoriatic disease activity can also be determined based on Overall Lesion Severity (OLS) scale, percentage of total body surface area (BSA) affected by psoriasis, and psoriasis plaque thickness. For asthma, one indicator of therapeutic effect is a decrease in nonspecific airway hyperresponsiveness to methacholine challenges (basal and postallergen; see Examples), upon treatment by the method of the invention. Airway hyperresponsiveness can be measured by $FEV_1$ (volume of air that can be forced from the lungs in 1 second). For transplant or graft survival and function, therapeutic effectiveness can be measured, e.g., by the incidence of acute graft rejection, by graft function, and length of graft survival, as described in the Examples. Other indicators of therapeutic effect will be readily apparent to one having ordinary skill in the art and may be used to establish efficacy of the dose.

In the method of the invention, the first dose in followed by a second dose which is higher than the first dose, that is, contains a greater amount of the therapeutic compound. The first dose serves to condition the mammal to tolerate the higher second therapeutic dose. In this way, the mammal is able to tolerate higher doses of the therapeutic compound than could be administered initially. Also within the scope of the present invention are additional doses, which may be administered after the second dose. For example, an additional, third dose which is higher than or equal to the second dose and an additional fourth dose which is higher than or equal to the second or third dose are contemplated within the method of present invention.

In a further embodiment, the first dose may be repeated one or more times before the second higher dose is administered. The first dose may be administered, for example, one, two or three times, most preferably only one time before the second higher dose is administered.

The doses may be administered according to any time schedule which is appropriate for treatment of the disease or condition. For example, the dosages may be administered on a daily, weekly, biweekly or monthly basis in order to achieve the desired therapeutic effect and reduction in adverse effects. The dosages can be administered before, during or after the development of the disorder. For example, to prevent host versus graft or graft versus host rejection, the initial conditioning dose may be administered before, during or after transplantation has occurred. The specific time schedule can be readily determined by a physician having ordinary skill in administering the therapeutic compound by routine adjustments of the dosing schedule within the method of the present invention. The time of administration of the first and second dosages as well as subsequent dosages will be adjusted to minimize adverse effects while maintaining a maximum therapeutic effect. The occurrence of adverse effects can be monitored by routine patient interviews and adjusted to minimize the occurrence of side effects, in particular, fever, headache, nausea and/or vomiting by adjusting the time of the dosing. Any dosing time is to be considered to be within the scope of the present invention so long as the first conditioning dose of the non-depleting compound is administered followed by a second higher dose of the compound. For example, additional doses may be on a daily or weekly schedule followed by subsequent biweekly or monthly doses.

The dosage amount will depend on the specific disease or condition which is treated and can be readily determined using known dosage adjustment techniques by a physician having ordinary skill in treatment of the disease or condition. The dosage amount will generally lie with an established therapeutic window for the therapeutic compound which will provide a therapeutic effect while minimizing additional morbidity and mortality. Typically, therapeutic compounds will be administered in a dosage ranging from 0.001 mg/kg to about 100 mg/kg per dose, preferably 0.1–20 mg/kg. The preferred dose of about 0.1–20mg/kg is particularly useful for non-cell depleting compounds containing antibodies or fragments thereof.

Typically, the therapeutic compound used in the method of this invention is formulated by mixing it at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of antagonist, but preferably ranges anywhere from about 3 to about 8. Formulation in an acetate buffer at pH 5 is a suitable embodiment. Where the therapeutic compound is an anti-LFA-1 antibody (such as hu 1124), a suitable embodiment is a formulation at pH 6.0.

The therapeutic compound, e.g. an anti-LFA-1 antibody, for use herein is preferably sterile. Sterility can be readily accomplished by sterile filtration through (0.2 micron) membranes. Preferably, therapeutic peptides and proteins are stored as aqueous solutions, although lyophilized formulations for reconstitution are acceptable.

The therapeutic compound may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the time scheduling of administration, and other factors known to medical practitioners. The "therapeutically effective amount" of the therapeutic compound to be administered will be governed by such considerations, and is the minimum amount necessary to prevent, ameliorate, or treat the disease, for example an LFA-1-mediated disorder, including treating rheumatoid arthritis, psoriasis, multiple sclerosis, asthma, or prolonging survival of a transplanted graft. Such amount is preferably below the amount that is toxic to the host or renders the host significantly more susceptible to infections.

The therapeutic compound may be administered by any suitable means, including parenteral, subcutaneous, intraperitoneal, intrapulmonary, intranasal, and intralesional administration. Parenteral infusions include intramuscular, intravenous, intraarterial, intraperitoneal, or subcutaneous administration. Preferably the dosing is given by injections, most preferably intravenous or subcutaneous injections, depending in part on whether the administration is brief or chronic.

In another aspect of the invention, a method of downmodulating a cell surface receptor in a cell population in a mammal is provided by contacting a target mammalian cell displaying a receptor molecule on the surface thereof with a first dose of a ligand which binds to the receptor molecule and does not deplete the mammalian cell population; and then further contacting the mammalian cell population with a second dose of the ligand, wherein the second dose is higher than the first dose. Binding of the ligand to the cell surface receptor reduces the number of receptors on the surface of the cell even though the numbers of cells are not substantially reduced. This reduction in surface receptors is associated with reduced side effects such as reduced fever, headache, nausea and/or vomiting.

The non-cell depleting compound or ligand used in this method may be same as described above, and may be provided to the mammal in the same manner of administration, using the same dosing schedule and in the same dosage amounts as described above.

Another aspect of the invention is the treatment of an LFA-1 mediated disorder by administering to a mammal, preferably a human patient, in need of such a treatment a first conditioning dose of a compound which binds to lymphocyte surface receptor LFA-1; and administering a second therapeutic dose of the compound, where the second dose is higher than the first dose. This aspect of the invention is different than conventional dosing methods for the treatment of such diseases which generally treat with regularly spaced, even doses of a therapeutic compound. For example, the immunoadhesin LFA-3TIP, which is a recombinant dimeric protein consisting of the first extracellular domain of human LFA-3 fused to the hinge and CH2 and CH3 human IgG regions, has been administered in equal weekly doses of 0.005 mg/kg, 0.025 mg.kg, 0.050 mg/kg or 0.075 mg/kg. In a second study, patients received 0.05, 0.10 or 0.15 mg/kg in equal doses every four weeks (Krueger et al.). In contrast, the method of the invention provides a first conditioning dose and then a second therapeutic higher dose.

This method of dose scheduling conditions the patient to tolerate higher doses of the therapeutic compound than would be tolerated by the patient, particularly when there are adverse effects on the patients due to administration of the therapeutic compound. The low first dose of the method of the invention is useful for reducing the fever, headache, nausea, vomiting, etc. which often accompany an initial administration of a drug compound. However, it is possible to give a low first dose, within the scope of the invention, to patients who do not experience adverse effects on first administration.

The first dose conditions the patient to receive a second higher dose with a reduction in adverse effects which may be observed with higher doses of therapeutic compounds. Generally, as the dosage amount increases, the number of adverse effects also increases. The method of the invention allows administration of larger therapeutic doses more quickly and with fewer adverse effects. This improves the effectiveness of the therapy since the patient is able to tolerate larger doses and for a longer time since there are fewer unpleasant side effects.

Any compound which binds to a lymphocyte surface receptor LFA-1 and reduces the severity of symptoms or conditions associated with an LFA-1 mediated disease may be used in this embodiment of the invention. Preferred compounds are peptide or protein compounds, more preferably such compounds which are or which contain an antibody or fragment thereof or which are fusions to an antibody fragment such as an immunoadhesin. Particularly preferred compounds are anti-CD11a antibodies or compounds containing fragments thereof.

As described above, the dosage amount will depend on the specific LFA-1 mediated disease which is treated and can be readily determined using known dosage adjustment techniques by a physician having ordinary skill in treatment of these diseases. The dosage amount will generally lie within an established therapeutic window for the therapeutic compound which will provide a therapeutic effect while minimizing additional morbidity and mortality. Typically, therapeutic compounds will be administered in a dosage ranging from 0.001 mg/kg to about 100 mg/kg per dose, preferably 0.1–20 mg/kg. The preferred dose of about is particularly useful for compounds containing antibodies or fragments thereof.

The therapeutic compound for treatment of an LFA-1 mediated disease may be administered by any suitable means, including parenteral, subcutaneous, intraperitoneal, intrapulmonary, intranasal, and intralesional administration. Parenteral infusions include intramuscular, intravenous, intraarterial, intraperitoneal, or subcutaneous administration. Preferably the dosing is given by injections, most preferably intravenous or subcutaneous injections, depending in part on whether the administration is brief or chronic. As described above in more detail, the therapeutic compound for treatment of an LFA-1 mediated disease may be formulated, dosed, and administered in a fashion consistent with good medical practice.

Psoriasis is an inflammatory disease characterized by hyperproliferation of keratinocytes and accumulation of activated T cells in the epidermis and dermis of psoriatic lesions. The upregulation of ICAM-1 on keratinocytes and its interaction with T-cell LFA-1 in lesional skin indicate that treatment with an anti-CD11a antibody might interfere with the disease process in psoriasis.

Allergic asthma is characterized by the cardinal features of airway inflammation, reversible airway obstruction, and hyperresponsiveness. In people with allergic asthma, lymphocytes are believed to play a central role in the asthmatic inflammatory response to an inhaled allergen. Chronic asthma symptoms may result from continual activation of lung lymphocytes in response to chronic exposure to perennial allergens (e.g., house dust mite, dog dander, or cat hair) or from sequential exposure to seasonal allergens to which the patient is reactive.

Within minutes of an inhaled exposure to an aerosolized allergen, the patient with allergic asthma will experience an immediate response (the early asthmatic response or EAR), which is characterized by a fall in the volume of air that can be forced from the lungs in 1 second ($FEV_1$) over 0–2 hours. In most cases, this fall in $FEV_1$ is reversible by treatment with a β-agonist bronchodilator. Approximately 50% of these patients will go on to experience a second fall in $FEV_1$ (the late asthmatic response or LAR) 3–7 hours after the initial allergen exposure. LAR is associated with more pronounced airway inflammation and increased bronchial reactivity to nonspecific stimuli. Airway hyperresponsiveness to the non-allergen-specific challenge of methacholine is another cardinal feature of asthma. Hyperresponsiveness of the airways in response to low levels of methacholine is recognized by a decrease in $FEV_1$ and may be exacerbated by exposure of the airways to allergen, viral infection, or physical irritants. Aerosolized allergen bronchial challenge, or bronchoprovocation, can be performed in the laboratory in patients with allergic asthma and is useful and relevant as a model for the study of anti-asthma medications (Crescioli et al. 1991 Ann Allergy 66:245–51; Cockcroft et al., 1987, Am Rev Respir Dis 135:264–267; Ward et al. 1993, Am Rev Respir Dis 147:518–523.). Most drugs with proven efficacy in asthma management attenuate airway responses (EAR and/or LAR) to inhaled allergens administered in allergen bronchial challenges.

Interleukins (IL-5, IL-3) and granulocyte/macrophage colony stimulating factor are known to be important for eosinophil differentiation, maturation, adherence, activation, and degranulation. These cytokines are produced by T cells isolated from patients with asthma (Walker et al., 1991, J. Immunol. 146:1829–35). The T-cell products IL-4 and IL-13 are key mediators of inflammation, increasing IgE levels. Activated T cells are increased in peripheral blood, bronchoalveolar lavage, and bronchial biopsy specimens from patients with asthma (Azzawi et al. 1990, Am Rev Resp Dis 142:1407–13; Corrigan & Kay 1990, Am Rev Respir Dis 141:970–7). Lymphocytes are the predominant cell type identified in morphometric studies of submucosal biopsies obtained from patients with asthma (Djukanovic et al., 1992, Am Rev Respir Dis 145:669–74).

EXAMPLES

The method of the invention is exemplified by the treatment of psoriasis, asthma and kidney transplant rejection (LFA-1 mediated diseases) with a therapeutic compound (an antibody) which binds to a cell surface receptor (CD11a). These examples also provide a representative example of down modulating a cell surface receptor in a mammalian cell population, reducing side effects and of conditioning a mammal to tolerate high doses of a therapeutic compound.

Example 1

Phase 1 Multiple-dose, Dose-escalation Study of the Effects of hu1124 in Subjects with Moderate to Severe Psoriases. (HUPS249)

The study drug, hu 1124, is a known humanized anti-CD11a antibody [see WO 98/23761 (humanized MHM24 (Fab)-8); Werther WA, et al., Humanization of an anti lymphocyte fictional-associated antigen (LFA)-1 monoclonal antibody and re-engineering of the humanized antibody for binding to rhesus LFA-1. J Immunol 1996;157:4986–95). hu1124 is a humanized IgG1 version of a murine anti-CD11a monoclonal antibody, MHM24, which recognizes human and chimpanzee CD11a. Humanization of MHM24 was accomplished by grafting the murine complementarity determining regions (hypervariable region) into consensus human IgG1/K heavy- and light-chain sequences. For H and L chain V sequences of hu1124, refer to GenBank accession no. P_W62013 and P_W62017, respectively; sequences are also shown in FIG. 1 in Werther et al., 1996, and in FIGS. 1A and 1B in WO 98/23761, incorporated herein by reference).

The study drug, hu1124, was supplied as a single-use, clear, colorless, sterile, non-pyrogenic solution in a glass vial. Each vial contained 10 mL of solution at a concentration of 4 mg/mL in 10 mM sodium acetate pH 5.0, with 0.02% polysorbate 20, 0.1% sodium acetate trihydrate, and 4% mannitol. No preservative was added to the solution. All study drug was stored at 2–8° C. (35.6–46.4° F.). The study drug was administered to subjects by continuous intravenous infusion over 90 minutes into a peripheral vein. The amount of drug to be given was based on subject weight and the dosage group to which the subject was assigned.

Safety was assessed by adverse events, clinical laboratory assessments, and pre- and post-treatment vital signs. Immunological activity was monitored by testing for the effects on cell-mediated immunity reactions (delayed hypersensitivity), tetanus antibody responses, and lymphocyte subpopulations (flow cytometry). Efficacy was monitored by changes in clinical signs and symptoms of the disease (including Psoriasis Area and Severity Index, PASI, scores) and global changes compared with the baseline condition. Skin biopsies were studied for the effects of hu1124 on lymphocytes within psoriatic lesions. Pharmacokinetics of the study drug were assessed by serial monitoring of plasma samples for hu1124 throughout the 98 days following the start of the study.

Thirty-nine subjects with moderate to severe plaque psoriasis were enrolled at eight study centers. The subjects included Caucasian, Black, Asian and Hispanic subjects. The subjects ranged in age from 26 to 73 years, with only one subject older than 70. Subject weight ranged from 65 to 122 kg. Between 15 to 72%, overall median of 33%, of the body surface area was psoriatic for the subjects enrolled in this study. Baseline PASI scores ranged from 15 to 42, with an overall median of 23 for the 39 subjects in this study. Each of the 39 subjects received multiple doses of hu1124, ranging from 0.1–1.0 mg/kg, administered by intravenous infusion. Of the 39 subjects, 10 were enrolled in one of the 0.1 mg/kg dose groups (four in the 0.1 mg/kg administered every two weeks dose group and six in the 0.1 mg/kg/wk dose group), 17 were enrolled in the 0.3 mg/kg/wk dose group, six were enrolled in the 0.3–0.6 mg/kg/wk dose group, and six were enrolled in the 0.3–1.0 mg/kg/wk dose group. All but five subjects completed the study. All subjects were evaluated for safety and efficacy. The table below shows the treatment schedule and number of patients in each arm of the study.

TABLE 1

Dose Escalation (mg/kg) and Treatment Schedule

|  | n | Day 0 | Day 7 | Day 14 | Day 21 | Day 28 | Day 35 | Day 42 |
| --- | --- | --- | --- | --- | --- | --- | --- | --- |
| Group A | 4 | 0.1 | — | 0.1 | — | 0.1 | — | 0.1 |
| Group B | 6 | 0.1 | 0.1 | 0.1 | 0.1 | 0.1 | 0.1 | 0.1 |
| Group C | 17 | 0.3 | 0.3 | 0.3 | 0.3 | 0.3 | 0.3 | 0.3 |
| Group D | 6 | 0.3 | 0.4 | 0.6 | 0.6 | 0.6 | 0.6 | 0.6 |
| Group E | 6 | 0.3 | 0.4 | 0.6 | 1.0 | 1.0 | 1.0 | 1.0 |

Results—Safety

The first-dose acute adverse events were primarily fever (reported by 17/39 or 44% of subjects), headache (reported by 7/39 or 18% of subjects), nausea (reported by 5/39 or 13% of subjects), and vomiting (2/39 or 5% of subjects). Acute (within 48 hours after dosing) adverse events of fever, headache, or vomiting after the first dose were not reported in subjects who received 0.1 mg/kg every other week or every week. The majority of acute adverse events were mild in severity. Importantly, the frequency of acute adverse events decreased with subsequent doses in each dose group.

Multiple infusions of hu1124 were safe and well-tolerated by the subjects in this study. The overall decreasing incidence of acute adverse events after the first dose in each dose group indicates that the acute adverse events are the result of initial drug exposure and not absolute drug level, which in turn indicates an adaptation or conditioning response to the "desensitizing" or "conditioning" dosing schedule of the invention.

Results—Pharmacokinetic/Pharmacodynamics

The mean peak and trough plasma levels of hu1124 appeared to be dose dependent and increased as the dose level of study medication increased. No accumulation of hu1124 was observed in the lower dose groups and a small degree of accumulation was observed after the maximum doses were infused in the higher dose groups. A decrease in CD11a expression was observed within 2–4 hours after study medication administration in all dose groups, with full recovery noted before the next dose in the lower dose groups and within 7–10 days after the hu1124 levels decreased to below detection levels. In the two highest dose groups, hu1124 binding sites remained saturated during the course of treatment.

A reversible increase in the average number of lymphocytes was observed in the higher dose groups after Day 7 with a return to the pretreatment numbers after dosing was completed. No effects on the distribution of T and B subtypes or decreases in T-cell subclasses were observed with any dose.

The tetanus antibody test results indicated that an established humoral antibody response, especially a second set IgG mediated antibody response, is able to persist in the presence of multiple doses of hu1124. Antibody response was evaluated in 36 of 39 patients by double antigen sandwich ELISA. No human anti-hu1124 antibody response was detected out to Day 98 after multiple weekly doses.

Results—Efficacy

Efficacy was based on the global assessment of improvement, PASI scores, and histological analysis of skin biopsies. Some clinical improvement ($\geq$poor improvement) was observed in 76% (29/38) of the subjects at Day 56. Of the subjects who received at least 0.3 mg/kg/wk, 64% (18/28) experienced clinical improvement of at least fair. Five subjects experienced an excellent improvement (i.e., 75–90% improvement from baseline), with higher rates of clinical improvement noted as the dose of study drug was escalated. Continuous improvement at Day 70 was observed in six subjects in the higher dose groups. Subjects infused with the higher doses of hu1124 had greater decreases in their PASI scores compared with subjects infused with the lower doses. Ten subjects had a 50% decrease in their PASI scores. A dose response as determined by decreasing PASI scores was noted in the higher dose groups at Day 28; however, by Day 56 no substantial differences were detected among the higher dose groups. Histological analysis of the skin biopsies revealed significant reduction in epidermal thickness and T-cell infiltration with clear anti-inflammatory effects and reversal of pathological epidermal hyperplasia in subjects treated with at least 0.3 mg/kg/wk.

Conclusions

The conclusions from this study of multiple, escalated infusions of hu1124 in subjects with moderate to severe plaque psoriasis are as follows:
(a) hu1124 was safe and well-tolerated in subjects who received multiple, escalated, infused doses ranging from 0.1 mg/kg/every two weeks to 1.0 mg/kg/wk;
(b) hu1124 provided clinical improvement in the majority of subjects as measured by global assessments, PASI scores, and histology;
(c) hu1124 reduced the CD11a levels on circulating lymphocytes;
(d) hu1124 did not affect an established humoral antibody response and did not elicit an immune response;
(e) hu1124 did not deplete lymphocyte counts; lymphocyte counts increased during higher dose treatment.

EXAMPLE 2

A Single-Dose and Multinle-Dose, Escalating Dose Study to Evaluate the Safety, Pharmacokinetics, and Biological Activity of Subcutaneously Administered hu1124 in Subjects with Moderate to Severe Plaque Psoriasis (HUPS254)

This study assessed the safety, pharmacokinetics and pharmacodynamics, and biological activity of hu1124 administered by subcutaneous injection in a single dose and in multiple doses to subjects with moderate to severe plaque psoriasis.

The study drug, hu1124, was the same as used in Example 1. It was supplied as single use vials containing 100 milligrams of sterile, pyrogen-free, lyophilized drug product which contains hu1124 antibody at a concentration of 100 mg/mL and 0.02 mmole L-histidine, and 0.96 mmole β,β-trehalose, pH 6.0 when reconstituted with 1.0 mL of sterile water for injection.

Twenty-six subjects received hu1124 subcutaneously. Subjects in Group A (n=2) received a single injection of 0.3 mg/kg of hu1124. Subjects in Groups B through E (n=24) received eight weekly injections in doses ranging from 0.5–2.0 mg/kg of hu1124.

Table 2 below shows the treatment schedule and number of patients in each arm of the study.

TABLE 2

Dose Escalation and Treatment Schedule

| Dose mg/kg | n (Actual Enrollment) | Day 0 | Day 7 | Day 14 | Day 21 | Day 28 | Day 35 | Day 42 | Day 49 |
|---|---|---|---|---|---|---|---|---|---|
| Group A (0.3) | 2 | 0.3 | — | — | — | — | — | — | — |
| Group B (0.5) | 4 | 0.5 | 0.5 | 0.5 | 0.5 | 0.5 | 0.5 | 0.5 | 0.5 |
| Group C (0.5–1.0) | 6 | 0.5 | 0.7 | 1.0 | 1.0 | 1.0 | 1.0 | 1.0 | 1.0 |
| Group D (0.7–1.5) | 6 | 0.7 | 1.0 | 1.5 | 1.5 | 1.5 | 1.5 | 1.5 | 1.5 |
| Group E (1.0–2.0) | 8 | 1.0 | 1.5 | 2.0 | 2.0 | 2.0 | 2.0 | 2.0 | 2.0 |

Adverse events were reported and assessed in a manner similar to Example 1. Acute adverse events included headache, fever, chills, myalgia, nausea, and vomiting. Any of these adverse events occurring within 48 hours from the time of injection with hu1124 were considered acute. Safety was assessed by pre- and post-treatment examinations (including vital sign measurements), clinical laboratory assessments (including blood chemistries, hematology, and urinalysis), by examination of reported adverse clinical events, and by a hearing assessment. Evaluation of efficacy was based on PGA levels of improvements, changes in PASI scores, and histological analysis of skin biopsies at Day 56.

Results—Safety

Subcutaneous administration of hu1124 has been very well tolerated. No local cutaneous reaction has been observed. The incidence of acute adverse reactions (occurring within 48 hours) that were seen previously, after intravenous administration (Example 1, HUPS249), appeared to have decreased by approximately 50%. The low incidence of headache (mild) in eight of 26 subjects (31%) and fever (low grade) in two of 26 subjects (8%) was noteworthy. Use of the "desensitizing" or "conditioning" dosing schedule of the invention for dose administration has allowed the safe administration of up to 2 mg/kg with minimal acute adverse events.

Results—Efficacy

The study population was defined as subjects who had a history of and/or were considered for systemic therapy for chronic moderate to severe plaque-type psoriasis (BSA>15% and PASI>12) which had been diagnosed for at least six months and had been stable for at least three months.

On the basis of the Physicians' Global Assessment (PGA), and decreases in Psoriasis Area Severity Index (PASI) score, a clear benefit of hu1124treatment was seen.

Improvement in psoriasis as judged by the PGA suggests a dose response. In Group A, [single dose group (0.3 mg/kg)], no improvement was seen, as expected. Subjects in Groups B, C, and D showed some improvement at Day 56. The improvements were as follows: in Group B (0.5 mg/kg), 1 Excellent (75–99% improvement over baseline), 1 Slight (1–24% improvement), 2 Withdrawn; in Group C (0.5–1.0 mg/kg), 2 Good (50–74% improvement), 1 Fair (25–49% improvement), 3 Slight; in Group D (0.7–1.5 mg/kg), 1 Good, 1 Fair, 4 Slight. Subjects in Group E show the greatest amount of improvement. In this group, were 1 Excellent, 2 Good, 2 Fair, 2 Slight, and 1 Withdrawn. The response in Group E indicates that all subjects dosed with hu1124 showed some improvement (one subject withdrew at Day 7).

Psoriasis Area and Severity Index (PASI) scores decreased by an average of 10.9% in the single dose 0.3 mg/kg group, by 47.1% in the 0.5 mg/kg group, by 36.3% in the 0.5–1.0 mg/kg group, by 33.2% in the 0.7–1.5 mg/kg group and by 35.6%, in the 1.0–2.0 mg/kg group. In general, the higher the PGA, the greater the reduction in PASI score.

This study was later expanded to add 15 more subjects to Group C and 16 more to Group E. Thus, Group C had a final enrollment of 21 subjects and Group E had 24 subjects, adding to a total of 55 subjects enrolled at 10 study centers (Group A study was discontinued).

The data generated from the total pool of 55 subjects from the multiple dose groups showed the following results and observations. Substantial improvements in PGA and PASI scores were observed by Day 56. Of the 55 subjects in the multiple-dose groups, 45% experienced Good or better improvements in PGA (defined as an improvement of ≧50% of all clinical signs and symptoms of psoriasis compared to baseline) and 47% experienced at least a 50% decrease in PASI scores. Furthermore, 18% of these subjects experienced at least a 75% reduction in PASI scores by Day 56 and were categorized as treatment responders. Among the multiple dose groups, higher proportions of subjects in the 0.5–1.0 mg/kg and 1.0–2.0 mg/kg groups experienced Good or better improvement in PGA. Of note, one subject in the 1.0–2.0 mg/kg group experienced compete resolution of disease symptoms as assessed by PGA. Higher proportions of subjects in these two dose groups also experienced at least 50% reductions in PASI scores compared with subjects in the other dose groups.

Results—Summary

Administration of a subcutaneous formulation of hu1124 was well-tolerated at the site of injection. Clinical benefits were clearly seen with Fair, Good, and Excellent responses (PGA) observed in several dosing groups. The most significant benefits were seen in Group E (1.0–2.0 me/kg), in particular, where all subjects dosed (one subject withdrew) showed improvement as early as Days 28–42 of therapy.

Example 3

An Extended Duration, Multiple-Dose Study to Evaluate the Safety, Pharmacokinetics, and Biological Activity of Intravenously and Subcutaneously Administered hu1124 in Subjects with Moderate to Severe Plaque Psoriasis (HUPS256)

In this study, two treatment groups receive multiple intravenous doses of hu1124 from 0.3 mg/kg to 1.0 mg/kg, for 12 weeks. Each hu1124 dose will be administered one time weekly over a period of 90 minutes. Three treatment groups receive multiple subcutaneous doses of hu1124 from 0.7 to 4.0 mg/kg, injected one time weekly for 12 weeks.

For intravenous administration, the study drug, hu1124, is supplied as a single-use, clear, colorless, sterile, non-pyrogenic solution in a glass vial. Each vial contains 10 mL of solution at a concentration of 4 mg/mL in 10 mM sodium acetate pH 5.0, with 0.02% polysorbate 20, 0.1% sodium acetate trihydrate, and 4% mannitol. No preservative is added to the solution. All study drug is stored at 2–8° C. (35.6–46.4° F.). For subcutaneous administration, the study drug is supplied as single use vials containing 100 milligrams of sterile, pyrogen-free, lyophilized drug product which contains hu1124 antibody at a concentration of 100 mg/mL and 0.02 mmole L-histidine, and 0.96 mmole β,β-trehalose, pH 6.0 when reconstituted with 1.0 mL of sterile water for injection.

Table 3 below shows the treatment schedule and number of patients in each arm of the study.

TABLE 3

Treatment Schedule hu1124 (mg/kg)

| | DAY | | | | | | | | | | | | |
|---|---|---|---|---|---|---|---|---|---|---|---|---|
| | 0 | 7 | 14 | 21 | 28 | 35 | 42 | 49 | 56 | 63 | 70 | 77 |
| Dosing Schedule (Intravenous Adminisiration) | | | | | | | | | | | | |
| Group A (n = 6) | 0.3 | 0.3 | 0.3 | 0.3 | 0.3 | 0.3 | 0.3 | 0.3 | 0.3 | 0.3 | 0.3 | 0.3 |
| Group B (n = 10) | 0.3 | 0.6 | 1.0 | 1.0 | 1.0 | 1.0 | 1.0 | 1.0 | 1.0 | 1.0 | 1.0 | 1.0 |
| Dosing Schedule (Subcutaneous Administration) | | | | | | | | | | | | |
| Group C (n = 20) | 0.7 | 1.0 | 1.0 | 1.0 | 1.0 | 1.0 | 1.0 | 1.0 | 1.0 | 1.0 | 1.0 | 1.0 |
| Group D (n = 20) | 0.7 | 2.0 | 2.0 | 2.0 | 2.0 | 2.0 | 2.0 | 2.0 | 2.0 | 2.0 | 2.0 | 2.0 |
| Group E (n = 20) | 0.7 | 4.0 | 4.0 | 4.0 | 4.0 | 4.0 | 4.0 | 4.0 | 4.0 | 4.0 | 4.0 | 4.0 |

Safety is assessed by pre- and post-treatment examinations (including vital sign measurements), hearing assessments, clinical laboratory assessments (including blood chemistries, hematology, and urinalysis), antibody to hu1124 (HAHA), and by examination of reported adverse clinical events as in the previous examples. Pharmacokinetics are assessed using various ex vivo immunologic assays. Biological activity is assessed by changes in PASI.

Results

To date, 61 patients have been enrolled and the dosing has been well tolerated at all doses used in the study. One adverse event of local skin reaction has been reported among the 40 patients who have received SC doses up to 2.0 mg/kg. None of the 18 patients who have received SC doses up to 4.0 mg/kg have reported an adverse event of local skin reaction. Clinical benefits are seen with Fair, Good, and Excellent responses (PGA) observed. To date, anti-CD11a (hu1124) administered by SC injection appears to be safe, well tolerated, and exhibits promising biological and clinical activity.

Example 4

Phase III Study of Efficacy, Safety, and Tolerability of Subcutaneous Administration of hu1124 in Subjects with Moderate to Severe Plaque Psoriasis during Three Phases: First Treatment, Retreatment, and Extended Treatment (ACD2058 g)

Subjects receive 12 weekly doses of anti-CD11a (hu1124) or placebo administered by SC injection, as outlined in the Table of dosing schedule immediately below. The doses consist of an initial conditioning dose at a concentration of 0.7 mg/kg SC and weekly doses of 1.0 mg/kg administered SC or 2.0 mg/kg SC thereafter.

TABLE 4

Dosing Schedule

| | Day | | | | | | | | | | | | |
|---|---|---|---|---|---|---|---|---|---|---|---|---|---|
| | 0 | 7 | 14 | 21 | 28 | 35 | 42 | 49 | 56 | 63 | 70 | 77 |
| Low dose (mg/kg) | 0.7 | 1.0 | 1.0 | 1.0 | 1.0 | 1.0 | 1.0 | 1.0 | 1.0 | 1.0 | 1.0 | 1.0 |
| High dose (mg/kg) | 0.7 | 2.0 | 2.0 | 2.0 | 2.0 | 2.0 | 2.0 | 2.0 | 2.0 | 2.0 | 2.0 | 2.0 |

Anti-CD11a (hu1124) is supplied as in the above Examples 2 and 3. When reconstituted with 1.0 mL of Sterile Water for Injection (SWFI), each vial contains hu1124 at a concentration of 100 mg/mL, as well as polysorbate 20, L-histidine hydrochloride, and ββ-trehalose, at pH of 6.0.

Primary efficacy determinations are made on FT Day 84, which is the end of the First Treatment (FT) period. On FT Day 84, subjects are defined as responders, partial responders, or non-responders according to the following definitions: Responder: PASI has decreased ≧75% from FT Day 0; Partial responder: PASI has decreased ≧50% but <75% from FT Day 0; Non-responder: PASI has decreased <50% from FT Day 0.

This response to therapy determines whether subjects are assigned to the Observation (OB) or Extended Treatment (ET) period after completion of the FT Day 84 assessments. Subjects defined as responders enter the Observation (OB) period and are followed either for 6 months or until relapse, whichever occurs first. Relapse is defined as loss of 50% or more of the improvement in PASI achieved between FT Day 0 and FT Day 84 (see Section 4.5.3.a). At the time of relapse, subjects who received active drug during the First Treatment (FT) period enter the Retreatment (RT) period and are re-randomized in a 2:1 ratio to anti-CD11a or placebo, respectively. Subjects who received placebo during the First Treatment (FT) period and qualify as responders receive anti-CD11a during the Retreatment period. Despite re-randomization, subjects remain within the dose level group (low dose or high dose) assigned during the First Treatment (FT) period. During the Retreatment (RT) period, subjects receive a second course of treatment consisting of 12 weekly SC injections.

Subjects defined as partial responders or non-responders at the end of the First Treatment (FT) period are assigned to the Extended Treatment (ET) period. Subjects remain within the dose levels assigned in the First Treatment (FT) period. Subjects who had received anti-CD11a in the First Treatment (FT) period are re-randomized 2:1 to anti-CD11a or placebo, respectively. All subjects who received placebo in the First Treatment (FT) period are assigned to anti-CD11a within their dose level. ET Day 0 occurs on the same day as FT Day 84: hence the two courses of study drug treatment are continuous over a 24-week period.

In a related study (ACD2062 g), subjects who had received prior anti-CD11a treatment and have antibodies to anti-CD11a, and subjects who are receiving concurrent topical psoriasis therapy or Ultraviolet B light (UVB) phototherapy are treated on the same dosing regimen as shown in the preceding table.

Efficacy, safety and tolerability are measured as described in the above examples.

Results

The above dosing regimen with initial, lower conditioning dose is well tolerated. Clinical benefits with Fair, Good, and Excellent responses (PGA) are observed.

Example 5

A Phase II Study to Evaluate the Safety and Efficacy of Anti-CD11a Antibody, hu1124, in Adults with Allergic Asthma Undergoing Aeroallero-provoked Bronchoconstriction (ACD2017 g)

This study evaluates the safety, tolerability, and efficacy of eight weekly SC (subcutaneous) injections of up to 2.0 mg/kg hu1124 in adult subjects with mild to moderate allergic asthma. The effect of hu1124 on early and late asthmatic response to an inhaled aeroallergen, and on both nonspecific and allergen-induced airway hyperresponsiveness, are evaluated. An initial low, conditioning dose of 0.7 mg/kg is administered followed by subsequent dosing at 2.0 mg/kg.

Thirty-six subjects with allergic asthma, ages 18–60 years, are treated in this study. Cutaneous responses to allergen (screened by skin prick testing and assessed by endpoint titration) are measured, and methacholine bronchial challenges are conducted. These data are used to estimate the starting allergen dose for use in allergen bronchial challenge, using an empirically derived and validated formula.

During the treatment period, study drug (hu1124 or placebo) is administered weekly by SC injection, for eight doses over 50 days (one dose per week). The first dose of study drug is administered on Day 0. Subjects undergo allergen bronchial and methacholine challenges. Methacholine challenges, measuring nonspecific airway hyperresponsiveness (basal and post-allergen), are performed the day prior to a scheduled allergen challenge and ~24 hours following the start of allergen challenge.

The hu1124 antibody is supplied by Genentech as a sterile, pyrogen-free, lyophilized drug product in 10-mL glass vials. When reconstituted with 1.0 mL of Sterile Water for Injection (SWFI), each vial contains hu1124 at a concentration of 100 mg/mL, 20 mmol of L-histidine, 240 mmol of β,β-trehalose, 0.04% polysorbate 20 (pH of 6.0). The placebo formulation has the same product composition but does not contain hu1124. Study drug is administered by SC injection in the forearm, thigh, or abdomen. The dosing regimen is shown in the table immediately below.

TABLE 5

Dosing Regimen

| Treatment | Day | | | | | | | |
|---|---|---|---|---|---|---|---|---|
| | 0 | 7 | 14 | 21 | 28 | 35 | 42 | 49 |
| hu1124 | 0.7 | 2.0 | 2.0 | 2.0 | 2.0 | 2.0 | 2.0 | 2.0 |
| Placebo | x | x | x | x | x | x | x | x |

Doses of hu1124 are given in mg/kg.

The safety and efficacy of hu1124 are assessed by the incidence and severity of adverse events, laboratory tests, physical examinations including vital signs, spirometry, and serum antibody response to hu1124 at baseline and during the treatment and follow-up periods. The incidence and magnitude of changes in hearing are assessed by audiograms. Efficacy measures include determining the change in LAR and EAR and allergen-induced increase in airway responsiveness. All subjects are followed for 28 days after dosing is complete.

Blood and urine samples are collected periodically for analysis of blood chemistries, hematology, and urinalysis. Specific parameters assessed are as follows: Chemistry: sodium, potassium, chloride, bicarbonate, glucose, BUN, creatinine, calcium, phosphorus, magnesium, total and direct bilirubin, albumin, ALT, AST, alkaline phosphatase, uric acid, total protein. Hematology: CBC with differential and platelet count. Urinalysis: complete urinalysis with microscopic examination. Serum antibodies to hu1124. Serum samples for pharnacokinetic evaluations. Vital sign measurement consists of sitting blood pressure, respiratory rate, pulse rate, and body temperature measured orally (° C.).

The above dosing regimen is well tolerated and shows efficacy in treating asthma.

Example 6

Phase I/II Study of Anti-CD11a (hu1124) for Renal Transplantation

The use of a non-T cell-depleting, humanized, monoclonal anti-CD11a antibody should cause significantly less toxicity, sensitization, and more specific immunosuppression than currently available anti-T cell monoclonal antibodies (OKT3).

This study evaluates the safety, pharmacokinetics and pharmacodynamics (PK/PD), biological activity and clinical effects of 12 weeks of subcutaneously administered anti-CD11a (hu1124) at 2 dose levels in patients undergoing their first cadaveric donor kidney transplant. Patients are treated with 12 doses at weekly intervals followed for 13 weeks. Each dose group has two arms in which standard background immunosuppression regimens are used, as summarized in Study Design Table 5 below. The immunosuppressive agents are cyclosporine, prednisone, mycophenolate mofetil (MMF) and sirolimus. Each patient receives the initial "conditioning" dose of anti-CD11a (hu1124) at 0.5 mg/kg or 0.7 mg/kg, dependent on dose group assignment, on Day 0 at least 1 hour prior to surgery as summarized in Table 6 below. Thereafter, each patient receives a maintenance dose of anti-CD11a (hu1124) at 0.5 mg/kg or 2.0 mg/kg each weekly visit for 11 weeks, based on the dose group.

TABLE 6

Study Design

| Dose Group | | n |
|---|---|---|
| Group I | Anti-CD11a (hu1124) 0.5 mg/kg plus | |
| Arm A. | Half-dose cyclosporine (2.5–5 mg/kg), sirolimus, prednisone | 9 |
| Arm B. | Full-dose cyclosporine (>5–10 mg/kg), MMF, prednisone | 9 |
| Group II | Anti-CD11a (hu1124) 2.0 mg/kg plus | |
| Arm A. | Half-dose cyclosporine (2.5–5 mg/kg), sirolimus, prednisone | 9 |
| Arm B. | Full-dose cyclosporine (>5–10 mg/kg), MMF, prednisone | 9 |

TABLE 7

Dosing Regimen

| Dose Group | Days of Study | | | | | | | | | | | |
|---|---|---|---|---|---|---|---|---|---|---|---|---|
| | 0 | 7 | 14 | 21 | 28 | 35 | 42 | 49 | 56 | 63 | 70 | 77 |
| Group I: 0.5 mg/kg | 0.5 | 0.5 | 0.5 | 0.5 | 0.5 | 0.5 | 0.5 | 0.5 | 0.5 | 0.5 | 0.5 | 0.5 |
| Group II: 2.0 mg/kg | 0.7 | 2.0 | 2.0 | 2.0 | 2.0 | 2.0 | 2.0 | 2.0 | 2.0 | 2.0 | 2.0 | 2.0 |

The study drug, anti-CD11a (hu1124), is supplied by XOMA as a sterile, pyrogen-free, lyophilized drug product in 10 mL glass vials which, when reconstituted with 1.0 mL Sterile Water for Injection (SWFI), contain anti-CD11a (hu1124) at a concentration of 100 mg/mL, 20 mmol of L-histidine, 240 mmol of α, α-trehalose, and 0.04% polysorbate 20 (pH of 6.0). Vials are refrigerated at 2° C.–8° C. (360° F.–46° F.) Reconstituted product is stable at room temperature for up to 8 hours.

Safety is assessed by the incidence of adverse events, vital signs, changes in laboratory values compared with baseline (hematology, chemistry, urinalysis), infections, lymphoma, acute rejection episodes, delayed graft function, graft loss, death, incidence of human anti-humanized monoclonal antibody (HAHA).

After initial dosing of the study drug in each patient, the pharmacokinetic characteristics of the study drug are assessed by serial measurement of plasma concentrations of anti-CD11a (hu1124) at various time points throughout the duration of the study. Flow cytometry analysis of T cells, T lymphocyte subsets (CD3/CD4/CD8), NK cells, and B lymphocytes, plus expression of CD11a on T lymphocytes, are performed.

Gene activation in cytotoxic T lymphocytes (perforin, granzyme B. FAS L) and cytokine gene expression (IL-10, IFN gamma, IL-2, TGF beta, IL-13) in urinary lymphocytes (Vasconcellos et al. 1998, Transplantation 66: 562–566) are examined. In addition, the humoral immune response is studied by examining peripheral blood for anti-HLA antibody production, by ELISA.

The biological activity is measured as follows. Alterations in graft function are assessed by serial measurements of serum creatinine, the need for dialysis during the initial 7 days post transplant, development of proteinuria, acute rejection episodes, and response to high-dose steroid therapy (as measured by serum creatinine). As per transplant center standard of care, graft biopsies are obtained at the time of implantation, when necessary to confirm the diagnosis of acute rejection, or if rejection does not occur, 1 week after treatment completion (Day 84). Material is obtained for cytokine and cytotoxic T lymphocyte mRNA analysis, quantitation of interstitial fibrosis, and other potential markers of chronic allograft nephropathy (i.e., collagen expression).

The above dosing regimen with an initial, lower conditioning dose of anti-CD11a antibody, followed by a higher therapeutic dose reduces the incidence of both acute graft rejection and delayed graft function, and promotes long-term survival with minimum toxicity, compared to the administration of equal doses throughout.

The method of the invention provides a higher therapeutic index than conventional and current therapy by minimizing toxicity and adverse side effects. The foregoing written specification is considered to be sufficient to enable one skilled in the art to practice the invention. Indeed, various modifications of the invention in addition to those shown and described herein will become apparent to those skilled in the art from the foregoing description and fall within the scope of the appended claims.

What is claimed is:

1. A method for treating an LFA-1 mediated disorder, comprising
    administering to a mammal in need thereof a first conditioning dose of an antibody or a receptor binding fragment thereof which binds CD11a; and
    administering a second therapeutic dose of the compound, wherein the second dose is higher than the first dose;
    wherein the LFA-1 mediated disorder is selected from the group consisting of asthma, rejection of a transplanted renal graft and rejection by a transplanted renal graft.

2. The method of claim 1, wherein the antibody or a receptor binding fragment thereof binds to an extracellular domain of CD11a.

3. The method of claim 1, wherein the antibody is a humanized antibody.

4. The method of claim 1, further comprising administering a third therapeutic dose, wherein the third dose is higher than or equal to the second dose.

5. The method of claim 4, further comprising administering a fourth therapeutic dose, wherein the fourth dose is higher than or equal to the third dose.

6. The method of any one of claims 1, 2, 3, 4, and 5, wherein administration is intravenous or subcutaneous.

7. The method of claim 6, wherein administration is not more than once per week.

8. The method of claim 7, wherein the antibody or a receptor binding fragment thereof is non-lymphocyte depleting.

9. The method of claim 8 wherein the lymphocyte is a T lymphocyte.

* * * * *